(12) United States Patent
Hirohara

(10) Patent No.: US 7,360,894 B2
(45) Date of Patent: Apr. 22, 2008

(54) OPTHALMOLOGICAL APPARATUS

(75) Inventor: Yoko Hirohara, Tokyo (JP)

(73) Assignee: Kabushiki Kaisha Topcon, Tokyo (JP)

( * ) Notice: Subject to any disclaimer, the term of this patent is extended or adjusted under 35 U.S.C. 154(b) by 309 days.

(21) Appl. No.: 11/090,310

(22) Filed: Mar. 28, 2005

(65) Prior Publication Data
US 2005/0219461 A1  Oct. 6, 2005

(30) Foreign Application Priority Data
Mar. 30, 2004 (JP) ............... 2004-099708

(51) Int. Cl.
*A61B 3/10* (2006.01)
(52) U.S. Cl. .................... 351/205
(58) Field of Classification Search ........ 351/205
See application file for complete search history.

(56) References Cited

U.S. PATENT DOCUMENTS

| 5,892,567 A * | 4/1999 | Hosoi et al. ........... 351/211 |
| 6,217,172 B1 * | 4/2001 | Shibutani et al. ........ 351/204 |
| 6,659,613 B2 | 12/2003 | Applegate et al. |

FOREIGN PATENT DOCUMENTS

| JP | 07-100107 A | 4/1995 |
| JP | 2001-095760 A | 4/2001 |
| JP | 2001-120504 A | 5/2001 |
| JP | 2002-204785 A | 7/2002 |
| JP | 2002-209854 A | 7/2002 |
| JP | 2002-306416 A | 10/2002 |
| JP | 2002-306417 A | 10/2002 |

\* cited by examiner

*Primary Examiner*—Scott J. Sugarman
*Assistant Examiner*—DaWayne A Pinkney
(74) *Attorney, Agent, or Firm*—Foley & Lardner LLP

(57) ABSTRACT

In an ophthalmological apparatus, how scattering at an eye under measurement and a contact lens affects how the eye sees is shown by measuring scattering when the contact lens is worn and by comparing a retinal image obtained with aberration and the scattering taken into account and a retinal image obtained with only the aberration taken into account. An aberration measurement section obtains the aberration of the eye under measurement. An other-components measurement section obtains other components other than the aberration component based on a point light-source image caused by each Hartmann plate. A scattering-level calculation section obtains a coefficient expressing the level of scattering based on the other components and the aberration. A simulation section generates a retinal image or data indicating how the eye under measurement sees with the measured aberration and the other components taken into account, based on the aberration and the coefficient.

10 Claims, 17 Drawing Sheets

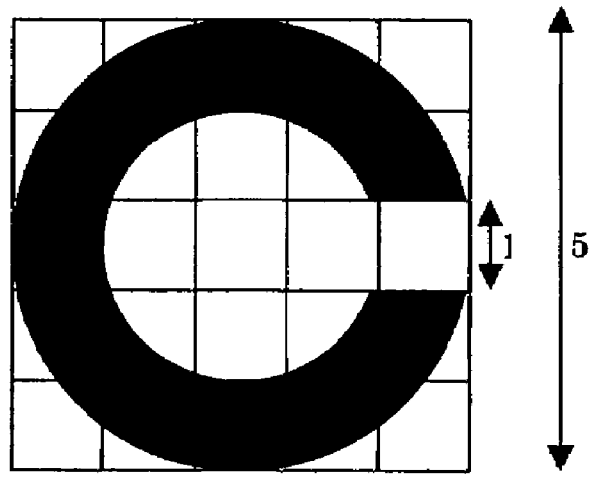
HIGH CONTRAST
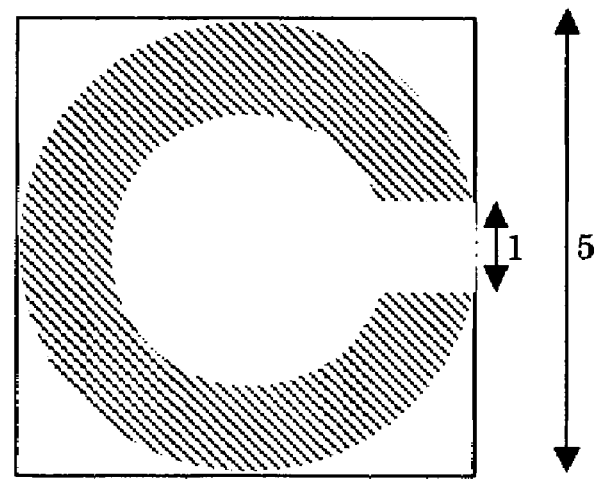
LOW CONTRAST
FIG.3

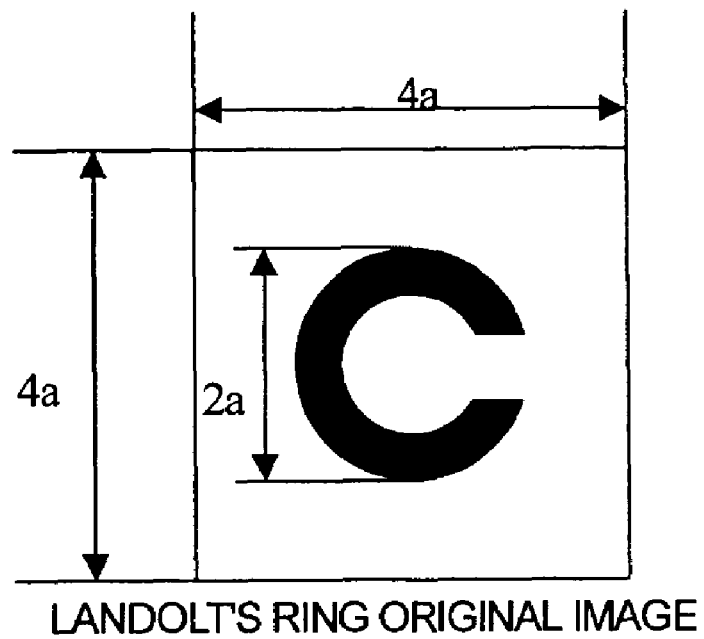
LANDOLT'S RING ORIGINAL IMAGE
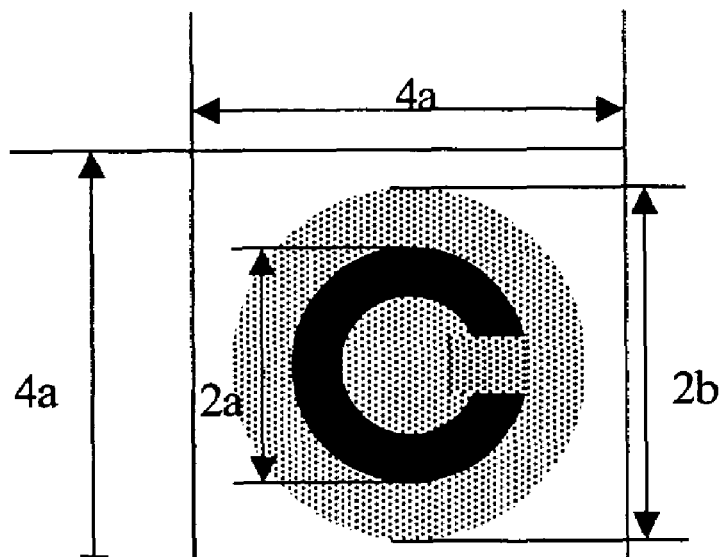
TEMPLATE IMAGE
FIG.9

[ABERRATION + SCATTERING] PUPIL DIAMETER: 4mm, CORRECTION DATA: S -4.25D C -1.0D A 3°

| MEASUREMENT DATE COMMENT | 2003.3.1 WHEN PURCHASED | 2003.3.21 TWO HOURS AFTER WORN | 2003.6.21 TWO HOURS AFTER WORN | 2003.9.27 TWO HOURS AFTER WORN | 2003.12.20 TWO HOURS AFTER WORN |
|---|---|---|---|---|---|
| VA 0.1 | | | | | |
| 0.5 | | | | | |
| 1.0 | | | | | |

| VISUAL ACUITY | ABERRATION ONLY | 1.5 | 1.5 | 1.5 | 1.2 | 1.2 |
|---|---|---|---|---|---|---|
| | ABERRATION + SCATTERING | 1.5 | 1.5 | 1.2 | 1.0 | 0.9 |
| TOTAL ABERRATION | | 0.53 | 0.56 | 0.60 | 0.86 | 0.89 |
| SCATTERING | | 5.7 | 7.2 | 9.5 | 9.7 | 10.3 |
| EVALUATION Index CHANGE | | 0 | 1.7 | 3.8 | 4.0 | 4.6 |

FIG.16

OPTHALMOLOGICAL APPARATUS

BACKGROUND OF THE INVENTION

1. Field of the Invention

The present invention relates to ophthalmological apparatuses.

2. Description of the Related Art

Conventionally, as a technique for measuring ocular correction data, measurement of S (Sphere), C (Cylinder) and A (axis) by a refractometer has been carried out. Besides, recently, an eye characteristic measuring apparatus capable of measuring higher order aberrations has also been developed, and not only S, C and A on a line like, for example, a ring of φ3 mm as in a refractometer, but also S, C and A on a plane when a pupil diameter is made various sizes can be calculated from lower order aberrations. By the eye characteristic measuring apparatus like this, especially after a refraction correcting surgical operation or in an eye disease, values closer to prescription values of eyeglasses or contact lenses than the refractometer can be calculated (for example, see Patent document 1-4 described followings etc.).

Apparatuses for displaying how a person under examination sees with a corrected eye or a naked eye have also been disclosed by the present applicant (in patent documents 5 and 6). In these apparatuses, for example, how a predetermined eyesight-test target is seen is displayed on display means according to the optical characteristics of an eye under measurement.

Patent document 1: Japanese Unexamined Patent Application Publication No. 2002-204785
Patent document 2: Japanese Unexamined Patent Application Publication No. 2002-209854
Patent document 3: Japanese Unexamined Patent Application Publication No. 2002-306416
Patent document 4: Japanese Unexamined Patent Application Publication No. 2002-306417
Patent document 5: Japanese Unexamined Patent Application Publication No. 2001-120504
Patent document 6: Japanese Unexamined Patent Application Publication No. Hei-7-100107

There have already been apparatuses capable of measuring eye aberration, as described above, and aberration measurement can be performed even when a contact lens is worn. How an eye under measurement sees have been evaluated by simulating a retinal image with the use of obtained aberration. In general, a point spread function (PSF) includes wavefront aberration and a scattering component. When the center of gravity of each spot is detected from a Hartmann image, only wavefront aberration is obtained even if scattering occurs.

In some cases, a stain on a contact lens, and the deterioration and dryness thereof largely affect how an eye under measurement sees, and if only the effect of aberration is taken into consideration, the measurement result is far away from how the eye under measurement actually sees. More specifically, if a Hartmann image blurs due to scattering caused by a stain on a contact lens, aberration does not change unless the center of gravity is changed, in wavefront aberration measurement which uses the Hartmann image. However, this scattering largely affects how the eye under measurement actually sees.

SUMMARY OF THE INVENTION

In view of the foregoing points, it is an object of the present invention to show how scattering at an eye and the contact lens affects how the eye sees by measuring scattering when the contact lens is worn and by comparing a retinal image obtained with aberration and the scattering taken into account and a retinal image obtained with only the aberration taken into account.

Another object of the present invention is to show how the current state of a contact lens affects how the eye sees by comparing retinal images obtained with the aberration and scattering of the eye taken into account, by using a measurement result obtained with the naked eye.

Still another object of the present invention is display how an eye sees affected by a stain on the contact lens and the deterioration and dryness thereof by subtracting measurement data obtained with the contact lens at a clean state from measurement data obtained with the contact lens after use.

According to the solving means of this invention, there is provided an ophthalmological apparatus comprising:

a first illumination optical system for projecting a point light source on the retina of an eye under measurement;

a first light-receiving optical system for receiving light reflected from the retina of the eye under measurement through a Hartmann plate:

a first light-receiving section for converting the received reflected light sent from the first light-receiving optical system into an electrical signal;

an aberration measurement section for obtaining the aberration of the eye under measurement from the output of the first light-receiving section;

an other-components measurement section for obtaining other components other than the aberration component, based on a point light-source image caused by each Hartmann plate, from the output of the first light-receiving section;

a scattering-level calculation section for obtaining a coefficient expressing a scattering level based on the aberration obtained by the aberration measurement section and the other components obtained by the other-component measurement section;

a simulation section for generating a retinal image or data indicating how the eye under measurement sees with the measured aberration and the other components being taken into account, based on the aberration obtained by the aberration measurement section and the coefficient obtained by the scattering-level calculation section; and a display section for displaying the retinal image or the data indicating how the eye under measurement sees, generated by the simulation section.

According to the present invention, how scattering at an eye and the contact lens affects how the eye sees can be shown by measuring scattering when the contact lens is worn and by comparing a retinal image obtained with aberration and the scattering taken into account and a retinal image obtained with only the aberration taken into account.

According to the present invention, how the current state of a contact lens affects how the eye sees can be shown by comparing retinal images obtained with the aberration and scattering of the eye taken into account, by using a measurement result obtained with the naked eye.

According to the present invention, how an eye sees affected by a stain on the contact lens and the deterioration and dryness thereof can be displayed by subtracting measurement data obtained with the contact lens at a clean state from measurement data obtained with the contact lens after use.

The present invention can be applied to ophthalmological apparatuses, ophthalmological application apparatuses, ophthalmological-operation apparatuses, and others.

BRIEF DESCRIPTION OF THE DRAWINGS

FIG. 3 is a view showing Landolt's rings.

FIG. 9 is a view showing template matching performed in step S1407.

FIG. 16 is a view showing RMS values, Index values, visual acuity, and simulation images with aberration only and the aberration and scattering taken into account, obtained at a plurality of measurement dates.

DESCRIPTION OF THE PREFERRED EMBODIMENTS

1. Eye Optical Characteristic Measuring Apparatus

Figure 1:
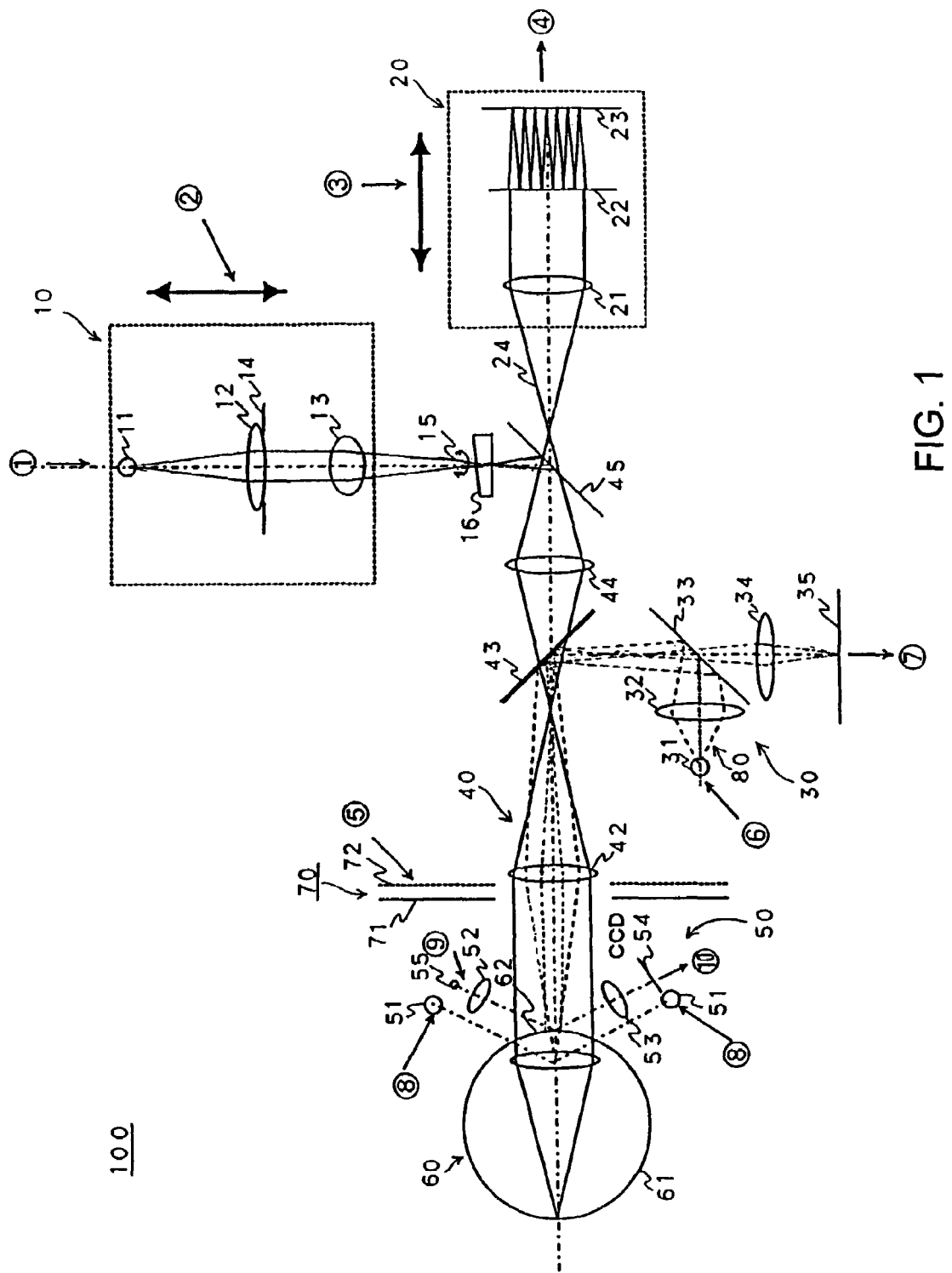
FIG. 1 is a view showing an outline optical system 100 of an eye-optical-characteristic measuring apparatus according to the present invention.

FIG. 1 is a view showing an outline optical system 100 of an eye optical characteristic measuring apparatus according to the present invention.

The optical system 100 of the eye optical characteristic measuring apparatus is, for example, an apparatus for measuring an optical characteristic of an eye 60 to be measured as an object, and includes a first illuminating optical system 10, a first light receiving optical system 20, a second light receiving optical system 30, a common optical system 40, an adjusting optical system 50, a second illuminating optical system 70, and a second light sending optical system 80.

Incidentally, with respect to the eye 60 to be measured, a retina 61 and a cornea 62 are shown in the drawing.

The first illuminating optical system 10 includes, for example, a first light source part 11 for emitting a light flux of a first wavelength, and a condensing lens 12, and is for illuminating a minute area on the retina (fundus) 61 of the eye 60 to be measured with the light flux from the first light source part 11 so that its illumination condition can be suitably set. Incidentally, here, as an example, the first wavelength of the illuminating light flux emitted from the first light source part 11 is a wavelength (for example, 780 nm) of an infrared range. It is not limited this wavelength, the light flux may be a light flux with predetermined wavelength.

Besides, it is desirable that the first light source part 11 has a high spatial coherence and a low temporal coherence. Here, the first light source part 11 is, for example, a super luminescence diode (SLD), and a point light source having high luminescence can be obtained. Incidentally, the first light source part 11 is not limited to the SLD, and for example, a laser having a high spatial coherence and a high temporal coherence can also be used by inserting a rotation diffused plate or the like to suitably lower the temporal coherence. Further, an LED having a low spatial coherence and a low temporal coherence can also be used, if light quantity is sufficient, by inserting, for example, a pinhole or the like at a position of a light source in an optical path.

To make a not-uniform characteristic of light reflected from the retina uniform, a wedge-shaped rotary prism (D prism) 16 is inserted into the illumination optical system. Since the rotation of the rotary prism changes the illumination portion on the eyeground, light reflected from the eye ground becomes uniform, and a light beam (point image) received by a light-receiving part is made uniform.

The first light receiving optical system 20 includes, for example, a collimator lens 21, a Hartmann plate 22 as a conversion member for converting a part of a light flux (first light flux) reflected and returned from the retina 61 of the eye 60 to be measured into at least 17 beams, and a first light receiving part 23 for receiving the plural beams converted by the Hartmann plate 22, and is for guiding the first light flux to the first light receiving part 23. Besides, here, a CCD with little readout noise is adopted for the first light receiving part 23, and as the CCD, a suitable type of CCD, for example, a general low noise type of CCD, a cooling CCD of 1000*1000 elements for measurement, or the like is applicable.

The second illuminating optical system 70 includes a second light source 72 and a Placido's disk 71. Incidentally, the second light source 72 can be omitted. The Placido's disk (PLACIDO'S DISK) 71 is for projecting an index of a pattern composed of plural co-axial rings. Incidentally, the index of the pattern composed of the plural co-axial rings is an example of an index of a specified pattern, and a different suitable pattern can be used. Then, after an alignment adjustment described later is completed, the index of the pattern composed of the plural co-axial rings can be projected.

The second light sending optical system 80 is for mainly performing, for example, the alignment adjustment described later, and measurement and adjustment of a coordinate origin and a coordinate axis, and includes a second light source part 31 for emitting a light flux of a second wavelength, a condensing lens 32, and a beam splitter 33.

The second light receiving optical system 30 includes a condensing lens 34 and a second light receiving part 35. The second light receiving optical system 30 guides a light flux (second light flux), which is originated from the pattern of the Placido's disk 71 illuminated from the second illuminating optical system 70 and is reflected and returned from the anterior eye part or the cornea 62 of the eye 60 to be measured, to the second light receiving part 35. Besides, it can also guide a light flux, which is emitted from the second light source part 31 and is reflected and returned from the cornea 62 of the eye 60 to be measured, to the second light receiving part 35. Incidentally, as the second wavelength of the light flux emitted from the second light source part 31, for example, a wavelength different from the first wavelength (here, 780 nm) and longer (for example, 940 nm) than that can be selected.

The common optical system 40 is disposed on an optical axis of the light flux emitted from the first illuminating optical system 10, can be included in the first and the second illuminating optical systems 10 and 70, the first and the second light receiving optical systems 20 and 30, the second light sending optical system 80 and the like in common, and includes, for example, an afocal lens 42, beam splitters 43 and 45, and a condensing lens 44. The beam splitter 43 is formed of such a mirror (for example, a dichroic mirror) that the wavelength of the second light source part 31 is sent (reflected) to the eye 60 to be measured, and the second light flux reflected and returned from the retina 61 of the eye 60 to be measured is reflected, and on the other hand, the wavelength of the first light source part 11 is transmitted. The beam splitter 45 is formed of such a mirror (for example, a polarization beam splitter) that the light flux of the first light source part 11 is sent (reflected) to the eye 60 to be measured, and the first light flux reflected and returned from the retina 61 of the eye 60 to be measured is transmitted. By the beam splitters 43 and 45, the first and the second light fluxes do not mutually enter the other optical systems to generate noise.

The adjusting optical system 50 is for mainly performing, for example, a working distance adjustment described later, includes a third light source part 51, a fourth light source part 55, condensing lenses 52 and 53, and a third light receiving part 54, and is for mainly performing the working distance adjustment.

Next, the alignment adjustment will be described. The alignment adjustment is mainly carried out by the second light receiving optical system 30 and the second light sending optical system 80.

First, the light flux from the second light source part 31 illuminates the eye 60 to be measured as the object with the substantially parallel light flux through the condensing lens 32, the beam splitters 33 and 43, and the afocal lens 42. The reflected light flux reflected by the cornea 62 of the eye 60 to be measured is emitted as a divergent light flux such as is emitted from a point at the half of the radius of curvature of the cornea 62. The divergence light flux is received as a spot image by the second light receiving part 35 through the afocal lens 42, the beam splitters 43 and 33, and the condensing lens 34.

Here, in the case where the spot image on the second light receiving part 35 is outside the optical axis, the main body of the eye optical characteristic measuring apparatus is moved and adjusted vertically and horizontally, and the spot image is made to coincide with the optical axis. As stated above, when the spot image coincides with the optical axis, the alignment adjustment is completed. Incidentally, with respect to the alignment adjustment, the cornea 62 of the eye 60 to be measured is illuminated by the third light source part 51, and an image of the eye 60 to be measured obtained by this illumination is formed on the second light receiving part 35, and accordingly, this image may be used to make the pupil center coincide with the optical axis.

Next, the working distance adjustment will be described. The working distance adjustment is mainly carried out by the adjusting optical system 50.

First, the working distance adjustment is carried out by, for example, irradiating the eye 60 to be measured with a parallel light flux emitted from the fourth light source part 55 and close to the optical axis, and by receiving the light reflected from the eye 60 to be measured through the condensing lenses 52 and 53 by the third light receiving part 54. Besides, in the case where the eye 60 to be measured is in a suitable working distance, a spot image from the fourth light source part 55 is formed on the optical axis of the third light receiving part 54. On the other hand, in the case where the eye 60 to be measured goes out of the suitable working distance, the spot image from the fourth light source part 55 is formed above or below the optical axis of the third light receiving part 54. Incidentally, since the third light receiving part 54 has only to be capable of detecting a change of a light flux position on the plane containing the fourth light source part 55, the optical axis and the third light receiving part 54, for example, a one-dimensional CCD arranged on this plane, a position sensing device (PSD) or the like is applicable.

Next, a positional relation between the first illuminating optical system 10 and the first light receiving optical system 20 will be described in outline.

The beam splitter 45 is inserted in the first light receiving optical system 20, and by this beam splitter 45, the light from the first illuminating optical system 10 is sent to the eye 60 to be measured, and the reflected light from the eye 60 to be measured is transmitted. The first light receiving part 23 included in the first light receiving optical system 20 receives the light transmitted through the Hartmann plate 22 as the conversion member and generates a received light signal.

Besides, the first light source part 11 and the retina 61 of the eye 60 to be measured form a conjugated relation. The retina 61 of the eye 60 to be measured and the first light receiving part 23 are conjugate. Besides, the Hartmann plate 22 and the pupil of the eye 60 to be measured form a conjugated relation. Further, the first light receiving optical system 20 forms a substantially conjugated relation with respect to the cornea 62 as the anterior eye part of the eye 60 to be measured, the pupil, and the Hartmann plate 22. That is, the front focal point of the afocal lens 42 is substantially coincident with the cornea 62 as the anterior eye part of the eye 60 to be measured and the pupil.

Besides, the first illuminating optical system 10 and the first light receiving optical system 20 are moved together so that a signal peak according to the reflected light at the light receiving part 23 becomes maximum on the condition that the light flux from the first light source part 11 is reflected at a point on which it is condensed. Specifically, the first illuminating optical system 10 and the first light receiving optical system 20 are moved in a direction in which the signal peak at the first light receiving part 23 becomes large, and are stopped at a position where the signal peak becomes maximum. By this, the light flux from the first light source part 11 is condensed on the eye 60 to be measured.

Besides, the lens 12 converts a diffused light of the light source 11 into a parallel light. A diaphragm 14 is positioned at an optically conjugated position with respect to the pupil of the eye or the Hartmann plate 22. The diaphragm 14 has a diameter smaller than an effective range of the Hartmann plate 22, and the so-called single path aberration measurement (method in which aberrations of an eye have an influence on only the light receiving side) is established. In order to satisfy the above, the lens 13 is disposed such that the retina conjugated point of the real light beam coincides with the front focal position, and further, in order to satisfy the conjugated relation between the lens and the pupil of the eye, it is disposed such that the rear focal position coincides with the diaphragm 14.

Besides, after a light beam 15 comes to have a light path common to a light beam 24 by the beam splitter 45, it travels in the same way as the light beam 24 paraxially. However, in the single path measurement, the diameters of the light beams are different from each other, and the beam diameter of the light beam 15 is set to be rather small as compared with the light beam 24. Specifically, the beam diameter of the light beam 15 is, for example, about 1 mm at the pupil position of the eye, and the beam diameter of the light beam 24 can be about 7 mm (incidentally, in the drawing, the light beam 15 from the beam splitter 45 to the retina 61 is omitted).

Next, the Hartmann plate 22 as the conversion member will be described.

The Hartmann plate 22 included in the first light receiving optical system 20 is a wavefront conversion member for converting a reflected light flux into plural beams. Here, plural micro-Fresnel lenses disposed on a plane orthogonal to the optical axis apply in the Hartmann plate 22. Besides, in general, with respect to the measurement object part (the eye 60 to be measured), in order to measure a sphere of the eye 60 to be measured, third-order astigmatism aberrations, and other higher order aberrations, it is necessary to perform the measurement with at least 17 beams through the eye 60 to be measured.

Besides, the micro-Fresnel lens is an optical element, and includes, for example, a ring with a height pitch for each wavelength, and a blade optimized for emission parallel to a condensing point. The micro-Fresnel lens here is subjected to, for example, 8-level optical path length variation employing a semiconductor fine working technique, and achieves a high condensing efficiency (for example, 98%).

Besides, the reflected light from the retina 61 of the eye 60 to be measured passes through the afocal lens 42 and the collimate lens 21 and is condensed on the first light receiving part 23 through the Hartmann plate 22. Accordingly, the Hartmann plate 22 includes a wavefront conversion member for converting the reflected light flux into at least 17 beams.

Figure 2:
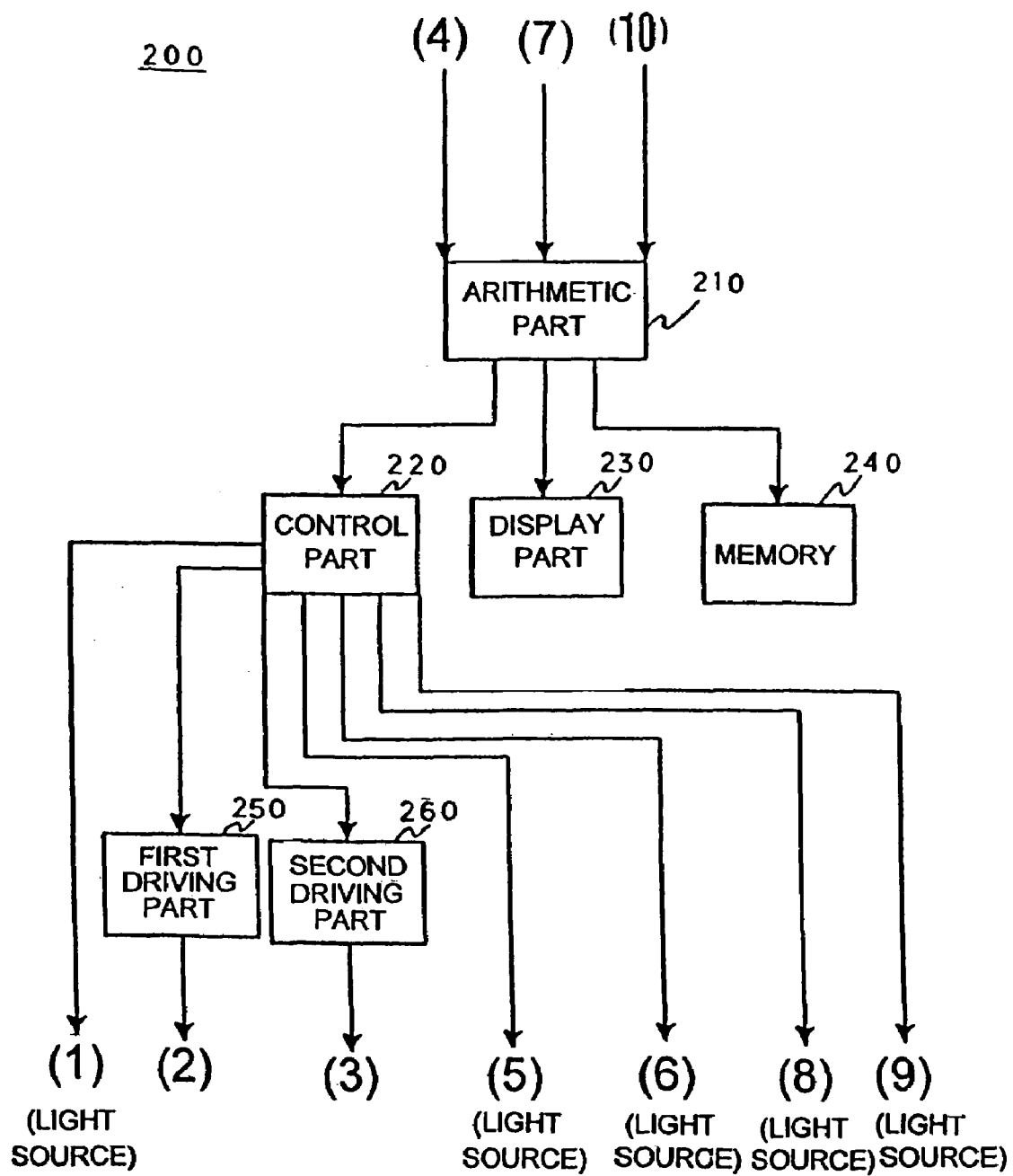
FIG. 2 is a block diagram showing an outline electrical system 200 of the eye-optical-characteristic measuring apparatus according to the present invention.

FIG. 2 is a block diagram showing an outline of electrical system 200 of the eye optical characteristic measuring apparatus related this invention. The electrical system 200 of the eye optical characteristic measuring apparatus includes, for example, an arithmetic part 210, a control part 220, a display part 230, a memory 240, a first driving part 250, and a second driving part 260.

The arithmetic part 210 receives a received light signal (4) obtained from the first light receiving part 23, a received light signal (7) obtained from the second light receiving part 35, and a received light signal (10) obtained from the third light receiving part 54, and performs an arithmetical operation on the origin of coordinates, a coordinate axis, movement of coordinates, rotation, ocular aberrations, corneal aberrations, Zernike coefficients, aberration coefficients, a Strehl ratio, a white light MTF, a Landolt's ring pattern and the like. Besides, signals corresponding to such calculation results are outputted to the control part 220 for performing the whole control of an electric driving system, the display part 230, and the memory 240, respectively. Incidentally, the details of the arithmetic part 210 will be described later.

The control part 220 controls lighting and extinction of the first light source part 11 on the basis of the control signal from the arithmetic part 210, or controls the first driving part 250 and the second driving part 260. For example, on the basis of the signals corresponding to the operation results in the arithmetic part 210, the control part outputs a signal (1) to the first light source part 11, outputs a signal (5) to the Placido's disk 71, outputs a signal (6) to the second light source part 31, outputs a signal (8) to the third light source part 51, outputs a signal (9) to the fourth light source part 55, and outputs signals to the first driving part 250 and the second driving part 260.

The first driving part 250 is for moving the whole first illuminating optical system 10 in the optical axis direction on the basis of, for example, the received light signal (4) inputted to the arithmetic part 210 from the first light receiving part 23, and outputs a signal (2) to a not-shown suitable lens movement means and drives the lens movement means. By this, the first driving part 250 can perform the movement and adjustment of the first illuminating optical system 10.

The second driving part 260 is for moving the whole first light receiving optical system 20 in the optical axis direction on the basis of, for example, the received light signal (4) inputted to the arithmetic part 210 from the first light receiving part 23, and outputs a signal (3) to a not-shown suitable lens movement means, and drives the lens movement means. By this, the second driving part 260 can perform the movement and adjustment of the first light receiving optical system 20.

The memory 240 includes a table having stored PSFs corresponding to coefficients (such as scatteing coefficient Index values, described later) indicating the levels of scattering, for each identifier identifying a contact lens.

Figure 17:
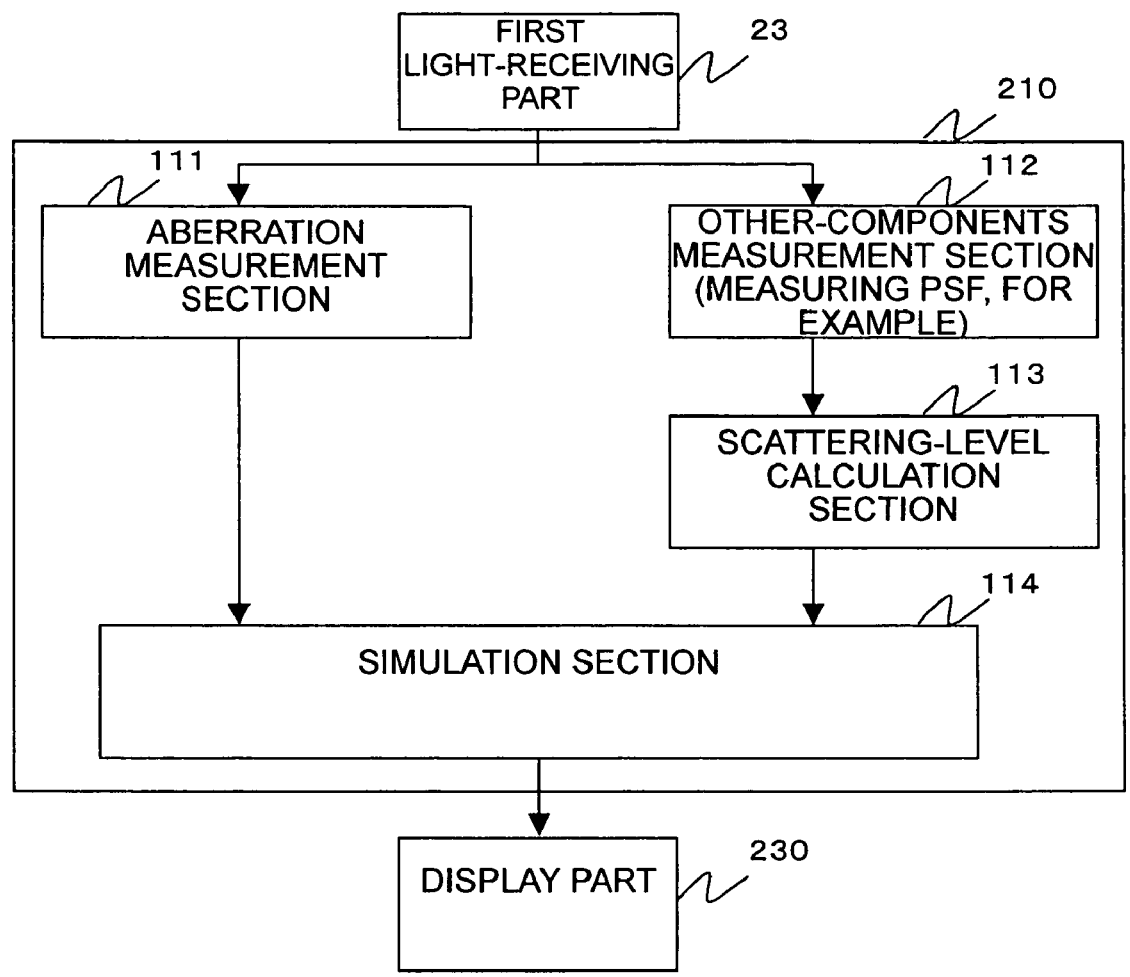
FIG. 17 is a view showing a detailed structure of an arithmetic part of the eye-optical-characteristic measuring apparatus.

FIG. 17 is a view showing a detailed structure of the arithmetic part 210 of the eye optical characteristic measuring apparatus. The arithmetic part 210 includes an aberration measurement section 111, an other-components measurement section 112, a scattering-level calculation section 113, and a simulation section 114.

The first light-receiving part 23 generates a first light-receiving signal from a light beam reflected from the eyeground of the eye under measurement, and leads it to the aberration measurement section 111 and the other-components measurement section 112.

The aberration measurement section 111 obtains optical characteristics (wavefront aberration and others) including the refractive power or cornea generation of the eye under measurement, based on the first light-receiving signal received from the first light-receiving part 23. The other-components measurement section 112 obtains other components other than the aberration component based on the point light-source image caused by each Hartmann plate from the output of the first light-receiving part 23. The scattering-level calculation section 113 obtains a coefficient expressing the level of scattering based on the other components obtained by the other-components measurement section 112 and the aberration obtained by the aberration measurement section 111.

The simulation section 114 generates data indicating how the eye under measurement sees with the measured aberration and the other components taken into account, based on the aberration obtained by the aberration measurement section 111 and the coefficient obtained by the scattering-level calculation section 113. The simulation section 114 references the memory 240 having stored point spread functions (PSFs) corresponding to coefficients (Index values) expressing the levels of scattering to obtain the PSF from the coefficient, and executes simulation based on the obtained PSF. The simulation section 114 also outputs the result of simulation on the display part 230. The display part 230 displays the data indicating how the eye under measurement sees, generated by the simulation section 114.

The simulation section 114 of the arithmetic part 210 obtains a visual-acuity simulation image by using the Index value by putting (for example, convolution integral) an experimental blur level obtained at the coefficient expressing the level of scattering or the PSF on the retinal image obtained with only the aberration taken into account. The blur of the PSF caused by scattering is uniquely determined, for example, for each coefficient expressing the level of scattering. The blur of the PSF increases as the coefficient expressing the level of scattering increases.

The memory 240 stores in advance PSF data for each coefficient Index expressing the level of scattering. The simulation section 114 references the memory 240 by the Index value to obtain the PSF, and convolution integral the obtained PSF into the retinal image calculated from the aberration to perform simulation. There are other methods. The average of the PSFs of a Hartmann image is convolution integral to simulate a retinal image. Alternatively, the scattering coefficient and cosine coefficient of a medium are calculated from the coefficient expressing the level of scattering and the PSF, and the results are used with the Monte Carlo method for calculating the probability of the transmission and direction of a light beam to simulate an image geometrically. The diameter of the pupil used in simulation may be a specified value (for example, 4 mm), or may be set to a value measured at an ordinary time. The visual acuity can be obtained to be compared with a visual acuity obtained when scattering is not taken into account.

The simulation section 114 can be configured so as to generate a retinal image or data indicating how the eye under measurement sees with the measured aberration taken into account, in addition to a retinal image or data indicating how the eye under measurement sees with the measured aberration and the other components, including the scattering component, taken into account. The simulation section 114 can also generate a simulation image of a retinal image or how the eye under measurement sees with the measured aberration taken into account, and a simulation image of a retinal image or how the eye under measurement sees with the measured aberration and other components, including the scattering component, taken into account, with the use of the measurement sections 111 and 112, and the display part 230 can display the simulation images generated by the simulation section 114. The simulation section 114 can further generate an estimated visual-acuity value of how the eye under measurement sees with the measured aberration taken into account, and an estimated visual-acuity value of how the eye under measurement sees with the measured aberration and other components, including the scattering component, taken into account, with the use of the measurement sections 111 and 112, and the display part 230 can display the estimated visual-acuity values generated by the simulation section 114.

Furthermore, when the eye under measurement is measured a plurality of times, the simulation section 114 can generate simulation images and/or data indicating a change in time of the eye under measurement, and the display part 230 can display the simulation images generated by the simulation section 114.

The simulation section 114 can generate data indicating how the eye under measurement sees based on a measurement result obtained in a naked-eye state and a measurement result obtained when a correction lens is worn, and the display part 230 can display the retinal images or data indicating how the eye under measurement sees based on the measurement result obtained in the naked-eye state and the measurement result obtained when the correction lens is worn, in a manner where comparison can be made. In this case, the simulation section 114 can generate a change in time of the retinal images or data indicating how the eye under measurement sees, and the display part 230 can display the change in time.

A change in time may be measured from a date when a certain period has elapsed from the date of purchase, or may be measured in units of hours from when the lens is worn.

The retinal image or data indicating how the eye under measurement sees includes data and images of optical characteristics of the eye under measurement (such as the visual acuity, the aberration, the scattering evaluation Index value, the diameter of the pupil, the PSF, the RMS, the Hartmann image, the Placido's-ring-image fixed image, the contrast, the change in each data, and others), simulation data, simulation images, and various types of data and images.

2. Zernike Analysis

Next, a Zernike analysis will be described. A generally known method of calculating Zernike coefficients $C_i^{2j-i}$ from Zernike polynomials will be described. The Zernike coefficients $C_i^{2j-i}$ are important parameters for grasping the optical characteristic of the subject eye 60 on the basis of inclination angles of the light fluxes obtained by the first light receiving part 23 through the Hartmann plate 22.

Wavefront aberrations W(X, Y) of the subject eye 60 are expressed using the Zernike coefficients $C_i^{2j-i}$ and the Zernike polynomials $Z_i^{2j-i}$ by the following expression.

$$W(X, Y) = \sum_{i=0}^{n} \sum_{j=0}^{i} c_i^{2j-i} Z_i^{2j-i}(X, Y)$$

Where, (X, Y) denotes vertical and horizontal coordinates of the Hartmann plate 22.

Besides, with respect to the wavefront aberrations W(X, Y), when the horizontal and vertical coordinates of the first light receiving part 23 are denoted by (x, y), a distance between the Hartmann plate 22 and the first light receiving part 23 is denoted by f, and a movement distance of a point image received by the first light receiving part 23 is denoted by (Δx, Δy), the following expression is established.

$$\frac{\partial W(X, Y)}{\partial X} = \frac{\Delta x}{f}$$

$$\frac{\partial W(X, Y)}{\partial Y} = \frac{\Delta y}{f}$$

Where, the Zernike polynomials $Z_i^{2j-i}$ are expressed by the following numerical expressions. (More specific expressions, for example, refer JP-A-2002-209854.)

$$Z_n^m = R_n^m(r) \left\{ \frac{\sin}{\cos} \right\} \{m\theta\}$$

$m > 0$ sin

-continued $$m \leq 0 \cos$$

$$R_n^m(r) \sum_{S=0}^{(n-m)/2} (-1)^S \frac{(n-S)!}{S!\left\{\frac{1}{2}(n-m)-S\right\}!\left\{\frac{1}{2}(n+m)-S\right\}!} r^m$$

Incidentally, with respect to the Zernike coefficients $C_i^{2j-i}$, specific values can be obtained by minimizing the squared error expressed by the following numerical expression.

$$S(x) = \sum_{i=1}^{data\ number} \left[\left\{\frac{\partial W(X_i, Y_i)}{\partial X} - \frac{\Delta x_i}{f}\right\}^2 + \left\{\frac{\partial W(X_i, Y_i)}{\partial Y} - \frac{\Delta y_i}{f}\right\}^2\right]$$

Where, W(X, Y): wavefront aberrations, (X, Y): Hartmann plate coordinates, (Δx, Δy): a movement distance of a point image received by the first light receiving part 23, f: a distance between the Hartmann plate 22 and the first light receiving part 23, m: the number of data.

The arithmetic part 210 calculates the Zernike coefficients $C_i^{2j-i}$, and uses this to obtain eye optical characteristics such as spherical aberrations, coma aberrations, and astigmatism aberrations.

(Normalization at the Diameter of the Pupil)

The Zernike polynomials always indicate a shape within a circle having a radius of 1. When Zernike analysis is performed at a pupil diameter, the Zernike polynomials are normalized at the radius of the pupil. When a pupil having a radius of $r_p$ has its center at coordinates (0, 0), for example, a point P(X, Y) within the pupil is expressed as P(X/$r_p$, Y/$r_p$) in Zernike analysis. When a spot of a Hartmann image has the center P of gravity, a reference grating point $P_{ref}(X_{ref}, Y_{ref})$ corresponding to the center P is expressed as $P_{ref}(X_{ref}/r_p, Y_{ref}/r_p)$, and the movement distance of a point image is obtained and the Zernike coefficients are calculated. An actual wavefront (wavefront where coordinates are not normalized) W(X, Y) is expressed by the following expression.

$$W(X, Y) = \sum_{i=0}^{n}\sum_{j=0}^{i} c_i^{2j-1} Z_i^{2j-1}(X/r_p, Y/r_p)$$

$$= \sum_{i=0}^{n}\sum_{j=0}^{i} c_i^{2j-1} Z_i^{2j-1}(x_s, y_s)$$

where, (X, Y) indicate coordinates not normalized, and ($x_s$, $y_s$) indicate normalized coordinates.

3. Landolt's Ring

FIG. 3 is a view showing Landolt's rings. How to generate data for the luminance spread function Land(x, y) of a Landolt's ring will be described below. In FIG. 3, a high-contrast Landolt's ring is shown at an upper part, and a low-contrast Landolt's ring is shown at a lower part.

The Landolt's ring is expressed by the reciprocal of a recognizable minimum visual angle, and the ability to be capable of recognizing a visual angle of one minute is called visual acuity of 20/20. For example, if the recognizable minimum visual angle is 2 minutes, the visual acuity is defined as 20/40, and if 10 minutes, the visual acuity is defined as 20/200. In general, the Landolt's ring uses, as an index, a ring in which a gap being ⅕ of the size of the outside ring is provided as shown in the drawing.

When the visual acuity is V, the size d of the Landolt's ring projected on the retina is calculated by $$d = 5 \times 2 \cdot R\tan\left(\frac{1}{60 \cdot V} \times \frac{1}{2}\right)$$

(R: a distance between a pupil and an image point (retina))

On the basis of this expression and the definition of the Landolt's ring, a black portion of the Landolt's ring is made 0 (or 1), a white portion thereof is made 1 (or 0), and the luminous distribution function Land(x, y) of the Landolt's ring is prepared. The data of the prepared luminous distribution function Land(x, y) is stored in the memory 240, is read out by the arithmetic part 210, and is set correspondingly to predetermined visual acuity.

As a high-contrast original image, for example, a Landolt's ring having a blank-and-white contrast of 100% (white is 0 while black is 1, for example) can be used. As a low-contrast original image, for example, a Landolt's ring having a black-and-white contrast of 10% (white is 0 while black is 0.1, for example) can be used. Original images having appropriate contrasts, other than the above examples, may be used. Luminance spread functions Land(x, y) are generated for a high-contrast image and a low-contrast image and stored in the memory 240.

4. Ophthalmological-Data Measurement Method

Figure 4:
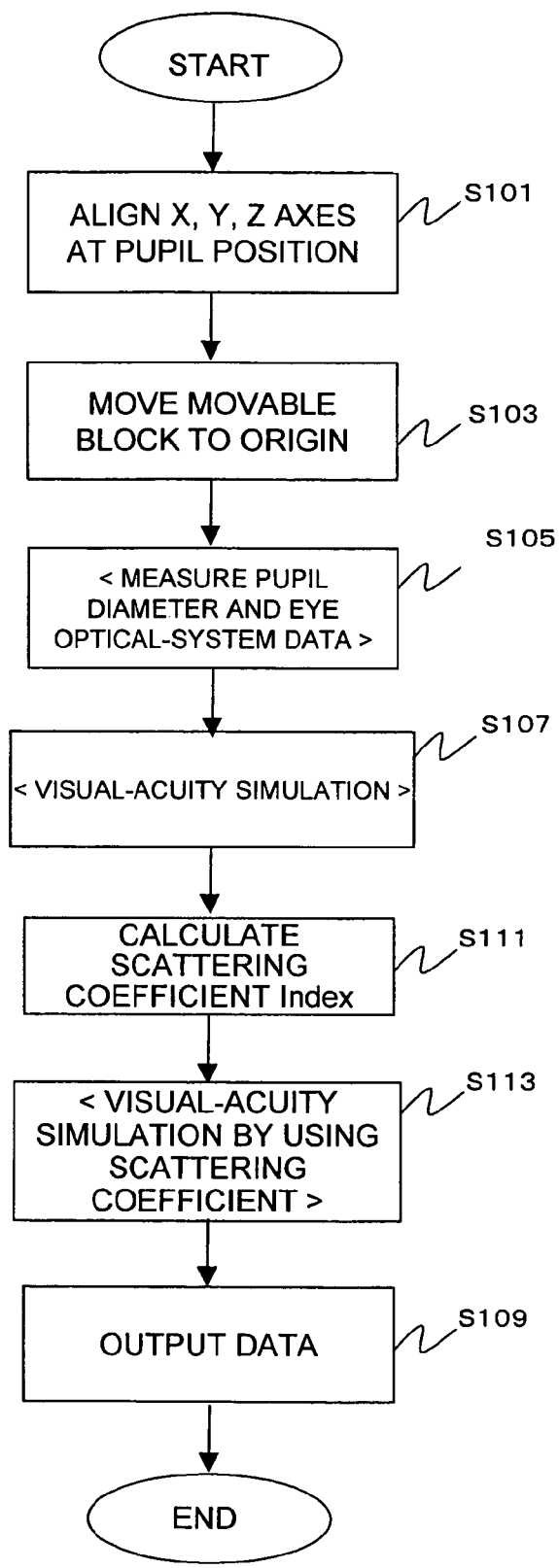
FIG. 4 is a flowchart of ophthalmological-data measurement.

FIG. 4 is a flowchart of ophthalmological-data measurement.

The eye-optical-characteristic measuring apparatus first aligns the X, Y, and Z axes at the pupil position of the eye 60 under measurement (S101). The measuring apparatus next moves a movable block to its origin (S103). For example, the Hartmann plate 22 and the Placido's ring 71 are adjusted to a diopter of zero. The arithmetic part 210 uses the aberration measurement section 111 to measure eye optical-system data such as a pupil diameter, the ocular aberration, and the Zernike coefficients according to the measured received-light signals (4), (7), and/or (10) (S105). Then, the arithmetic part 210 uses the other-components measurement section 112 to obtain other components (such as the modulation transfer function (MTF) and point spread function (PSF) of the eye under measurement) other than the aberration component, based on the point light-source images of the Hartmann plate by using the output of the first light-receiving part 23 (S105).

Next, the arithmetic part 210 uses the simulation section 114 to perform visual-acuity simulation (S107). For example, the arithmetic part 210 uses the result of comparison between a predetermined template and the result of simulation of how the eyesight-chart target is seen, and/or the MTF, which indicates the transfer characteristic of the eye under measurement, as an evaluation parameter indicating the quality of how the eye 60 under measurement sees, and estimates the visual acuity or sensitivity of the eye under measurement based on the evaluation parameter. As for the visual acuity, when eyesight-chart targets are appropriately specified, high-contrast visual acuity and low-contrast visual acuity can be estimated. Details of steps S105 and S107 will be described later. The calculation of the other components made by the other-components measurement section 112 in step S105 may be executed in a subsequent step, such as step S111 or S113.

Then, the arithmetic part 210 uses the scattering-level calculation section 113 to obtain a coefficient (such as a scattering coefficient Index) indicating the level of scattering (S111). More specifically, the scattering-level calculation section 113 obtains the average A in a range according to pupil diameter of the areas at the half magnitudes of the PSFs which is used when the scattering coefficient is obtained and the average wavefront aberration $RMS_{SL}$ of lenslets, and obtains the scattering coefficient Index by the following expression with the use of constants "a" and "c" determined in advance.

$$Index = \sqrt{A} - (a \cdot RMS_{SL} - c)$$

where Index is a scattering coefficient (scattering indicator), "A" indicates the average area at the half magnitudes of the PSFs, $RMS_{SL}$ indicates the average wavefront aberration of lenslets, "a" indicates a constant obtained from measurement of a not-cataractous eye, and "c" indicates a scattering calibration constant of the measuring apparatus.

Figure 13:
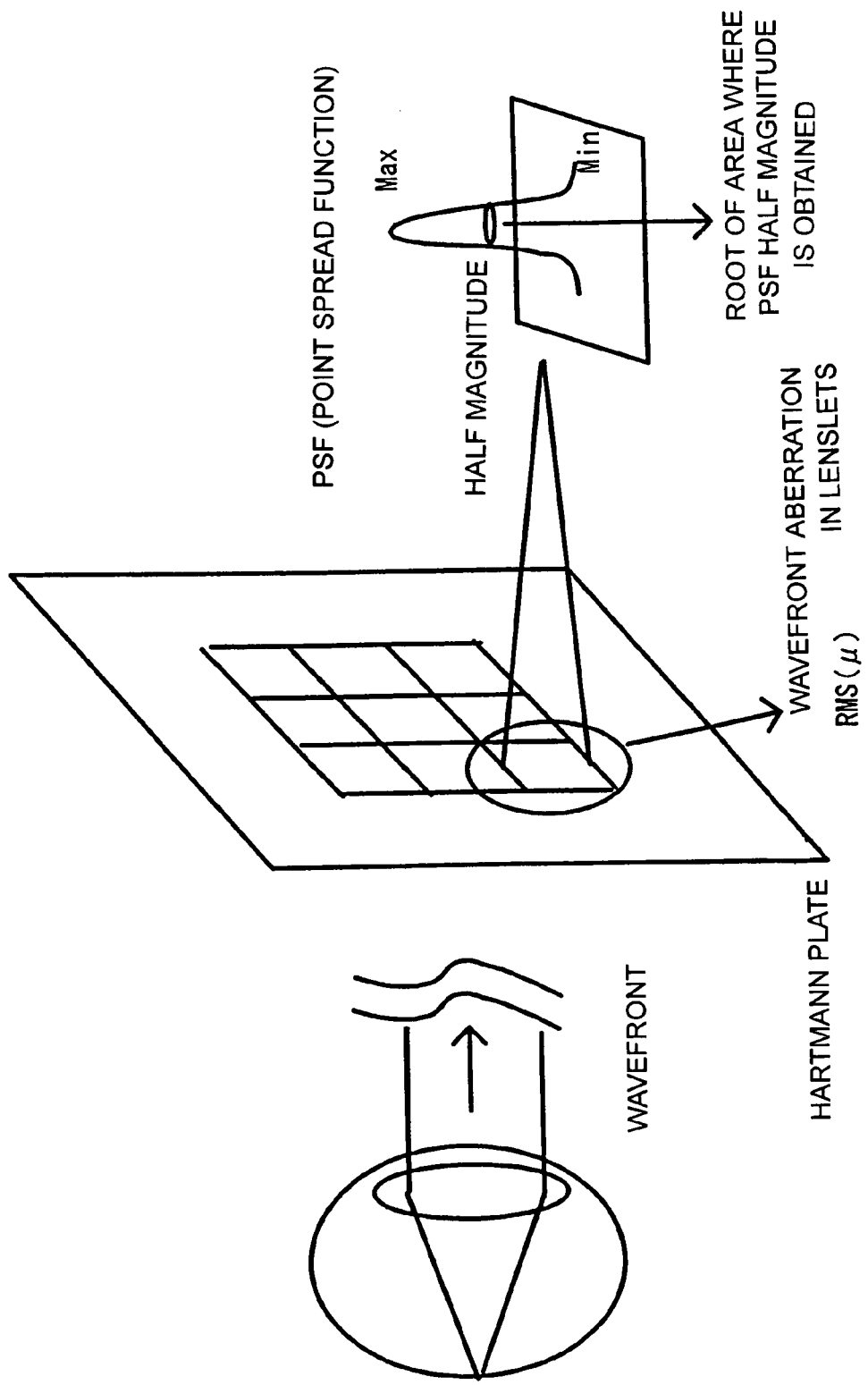
FIG. 13 is a view showing a scattering coefficient.

FIG. 13 is a view showing how the scattering coefficient Index is obtained.

The arithmetic part 210 uses the simulation section 114 to perform visual-acuity simulation by the use of the Index value in the same way as described above (S113). Details of step S113 will be described later.

The arithmetic part 210 outputs data (the visual acuity, the simulation image, and others) related to how the eye under measurement sees, obtained in steps S107 and S113 to the display part 230 and to the memory 240 (S109). When the data has been already output in a previous process, the process of step S109 may be omitted.

Figure 8:
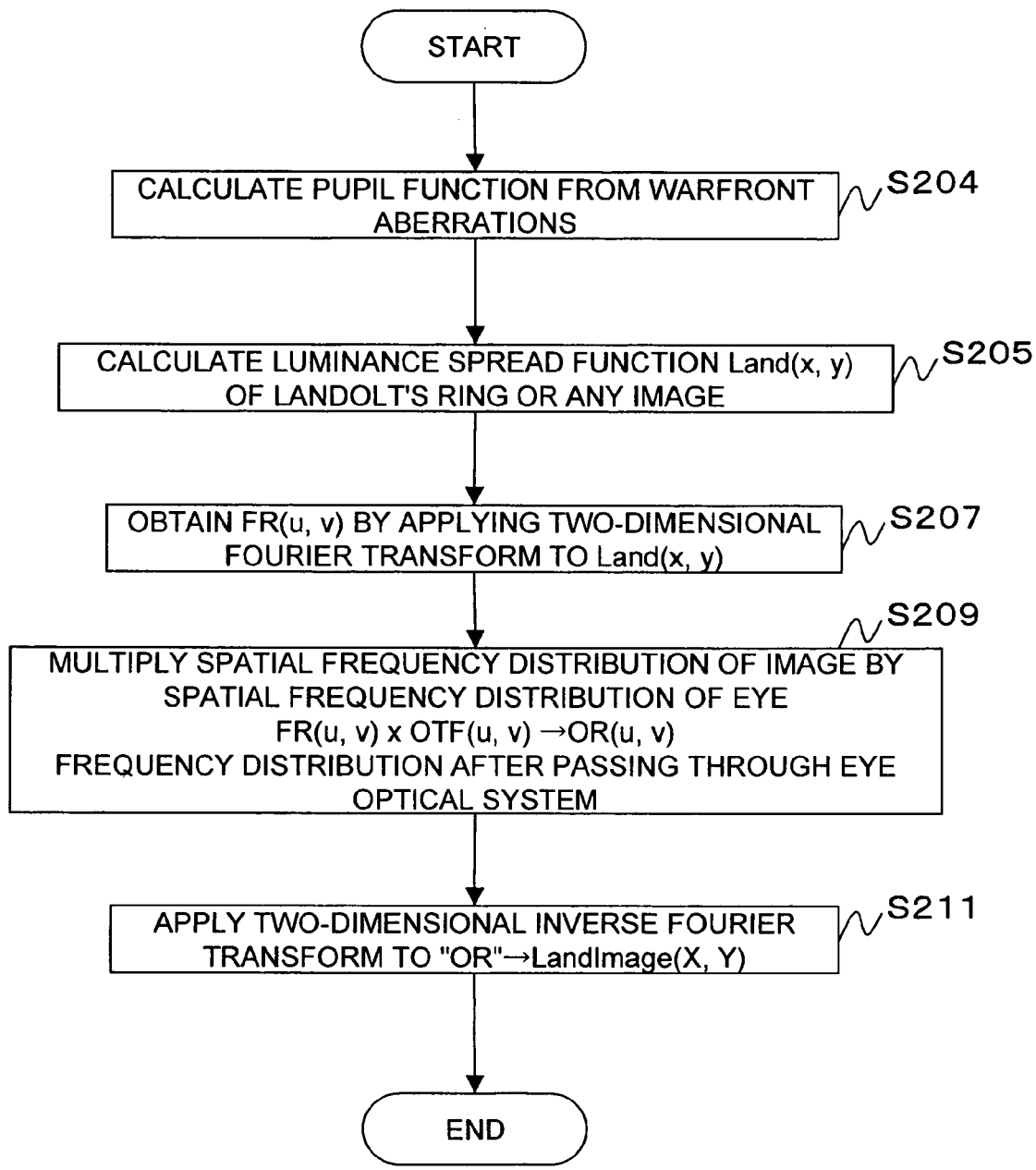
FIG. 8 is a flowchart of retinal image simulation performed in step S1405 when a scattering coefficient is not used.
Figure 12:
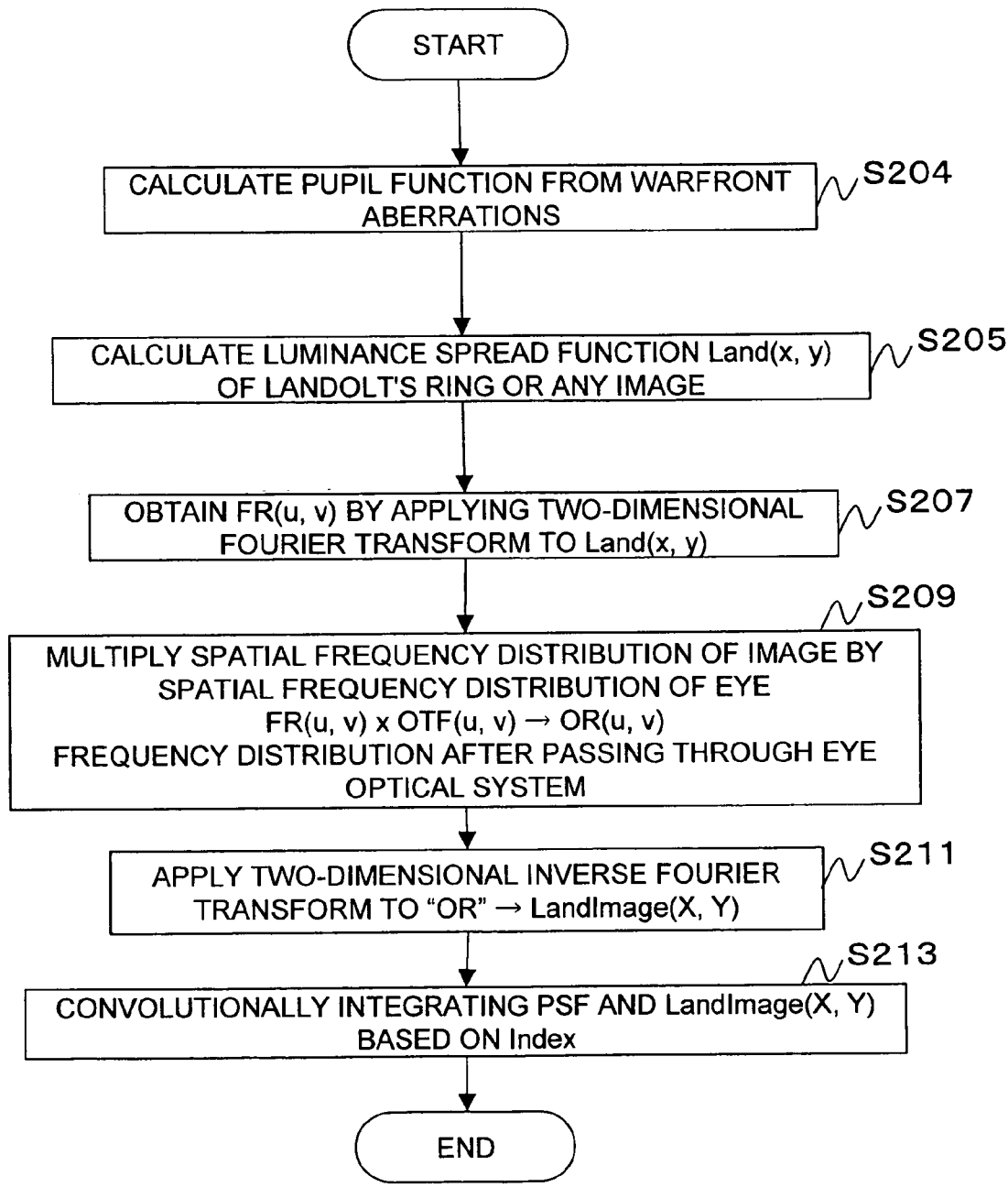
FIG. 12 is a flowchart of retinal image simulation performed in step S1405 when a scattering coefficient is used.

The process of step S107 and the process of step S113 are the same except that a flowchart shown in FIG. 8 is used for retinal image simulation in step S107 and a flowchart shown in FIG. 12 is used for retinal image simulation in step S113 in visual-acuity simulation to be described in 4-1.

The arithmetic part 210 can execute the processing shown in the flowchart of FIG. 4 before and after a contact lens is worn to obtain data used for comparing the states before and after the contact lens is worn and data related to how the eye under measurement sees, such as simulation images, and to display the data on the display part 230, or to output the data to the memory 240 and other apparatuses.

Figure 5:
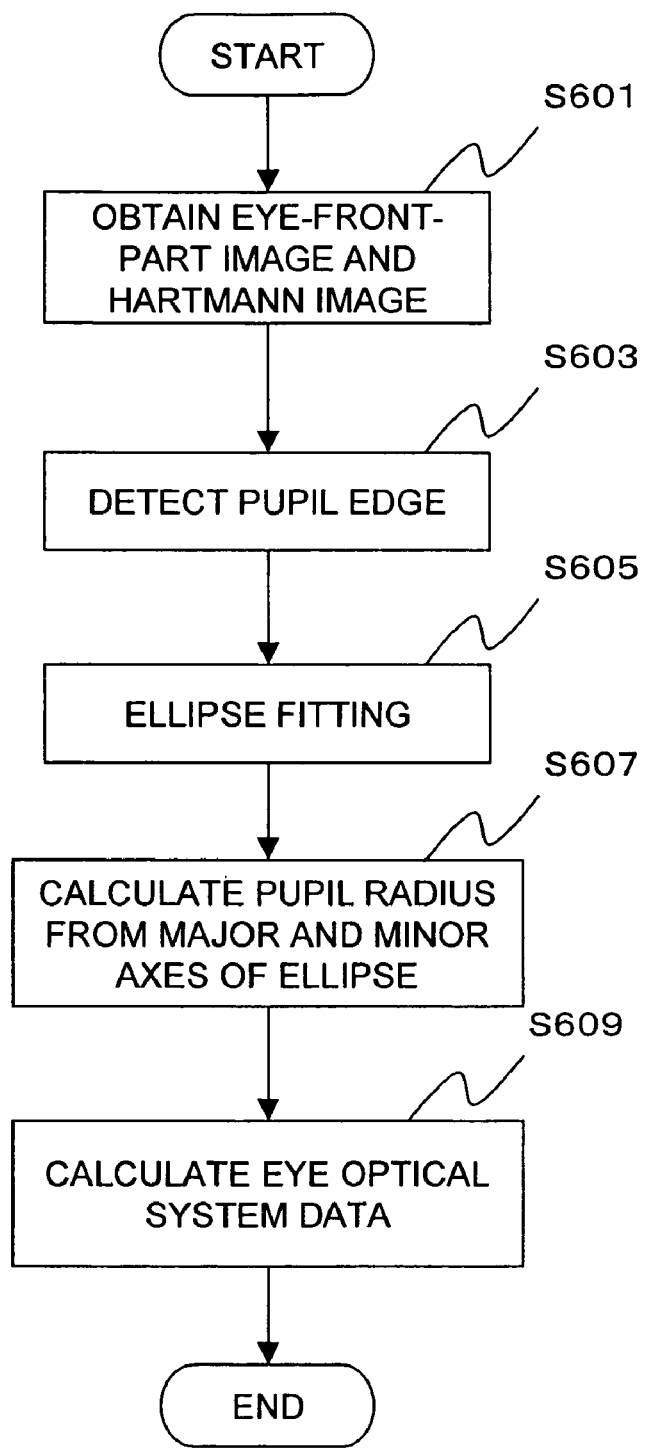
FIG. 5 is a flowchart of calculating a pupil diameter and measuring eye optical system data performed in step S105.
Figure 6:
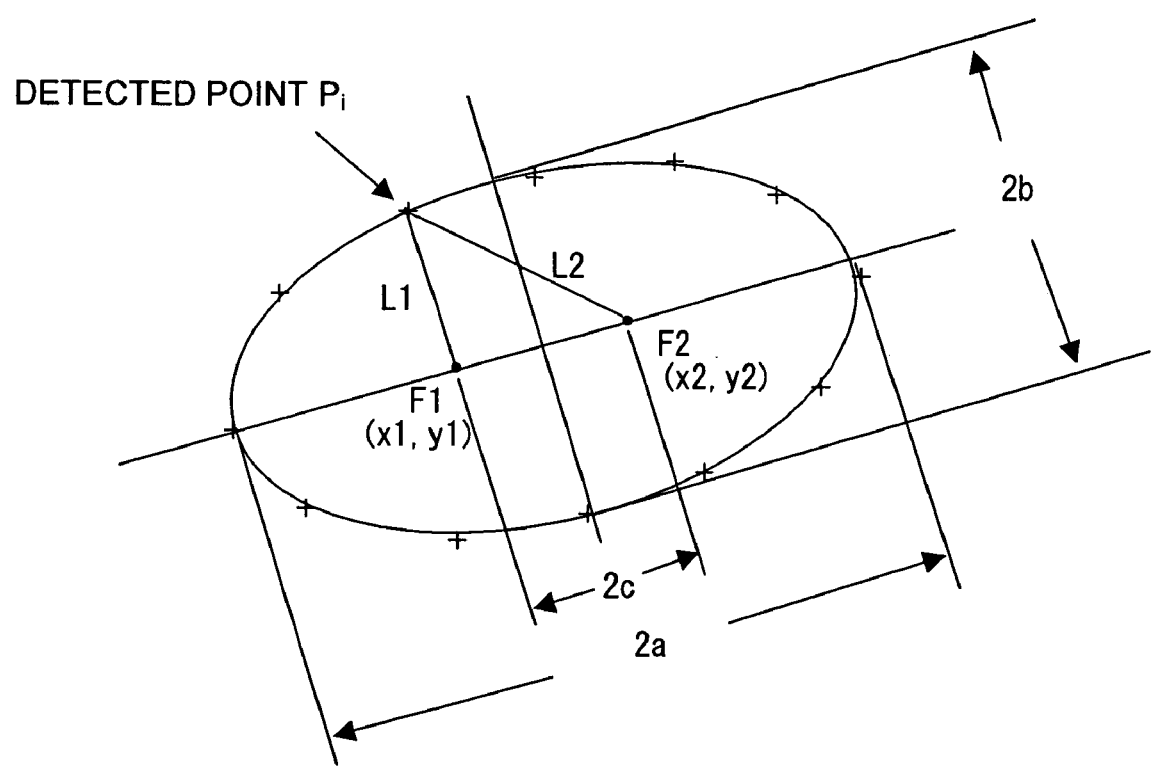
FIG. 6 is a view showing calculating a pupil diameter.

FIG. 5 is a flowchart of calculating a pupil diameter and measuring eye optical-system data, executed in step S105. FIG. 6 is a view showing how the pupil diameter is calculated.

The arithmetic part 210 first obtains the Hartmann image and the eye-front-part image from the first light-receiving part 20 and the second light-receiving part 35 (S601). More specifically, the arithmetic part 210 makes the fifth light-source part 91 illuminate the eye 60 under measurement in an illumination state specified by a desired environmental condition (observation condition), and obtains the Hartmann image and the eye-front-part image from the first light-receiving part 20 and the second light-receiving part 35. For example, the arithmetic part 210 displays on the display part 230 an instruction for selecting an environmental condition where the visual acuity or sensitivity is estimated, and a selected environmental condition is input from an input part 270. The environmental condition includes, for example, "daytime seeing", "twilight seeing", "indoors (under fluorescent light)", "nighttime seeing", and "usual visual-acuity measurement". Then, the arithmetic part 210 references, for example, a table in which environmental conditions and illumination states are associated with, stored in advance in the memory 240, and obtains the illumination state corresponding to the input environmental condition. An illumination state is specified for each environmental condition, such as 50 1x for "usual visual-acuity measurement", 100,000 1x for "daytime seeing", and 2,000 1x for "indoors (under fluorescent light)". These values can be appropriate values corresponding to the environmental conditions. It is desired that a larger fixation target than usual be used depending as an environment. In the present case, the fifth light-source part 91 illuminates the eye 60 under measurement in an illumination state specified by a desired environmental condition. The illumination state may be generated by using the illumination surrounding the eye under measurement or background illumination.

The arithmetic part 210 outputs a signal (11) corresponding to the obtained illumination state to the fifth light-source part 91 through the control part 220 to make the fifth light-source part 91 illuminate the eye 60 under measurement. The arithmetic part 210 can sequentially change the illumination state from a dark state to a bright state to obtain Hartmann images and eye-front-part images in a plurality of illumination states.

The arithmetic part 210 may skip step S601 and read Hartmann-image data, an eye-front-part image, pupil-diameter data which includes either a pupil shape, such as points on a pupil edge, or a pupil diameter, measured and stored in advance in the memory 240. Alternatively, for example, the arithmetic part 210 may read photographic data captured in the past and stored in the memory 240, the data being recorded in an electronic medical record as pupil-diameter data, from the memory 240 to obtain an eye-front-part image.

Then, the arithmetic part 210 detects, for example, 36 (n=36) points Pi (i=1 to n) on the pupil edge according to the obtained eye-front-part image (S603). More specifically, the arithmetic part 210 detects changes (image gradations) in the amount of light in the obtained eye-front-part image by using an image processing method to obtain points on the pupil edge. In FIG. 6, the detected points Pi are indicated by + signs.

Then, the arithmetic part 210 obtains an ellipse which fits the detected points on the pupil edge most (S605). The arithmetic part 210 first obtains the foci (points F1 and F2 in FIG. 6) of the ellipse. For example, the arithmetic part 210 reads the coordinates of two points specified in advance as the initial values of the foci, from the memory 240. Then, the arithmetic part 210 obtains the distances from each detection point Pi to the two read points, and obtains the sum Li of the distances. The arithmetic part 210 obtains the sum Li of the distances for all the detected points Pi, and obtains the average A of Li. Then, the arithmetic part 210 calculates two points where the square error Se of the sum Li of the distances and the average A, indicated by the following expression, becomes minimum by using the least square approximation or others to obtain the foci of the ellipse.

$$S_e = \sum_{i=1}^{n}(L_i - A)^2$$

where, Li indicates the sum of distances from a point Pi on the edge to the two points F1 and F2, "A" indicates the average of Li at each point on the edge, and "n" indicates the number of detected points on the edge. The foci of the ellipse may be obtained by an appropriate method other than that described above.

Next, the arithmetic part 210 obtains the sum L of distances from a point on the ellipse to the foci. The arithmetic part 210 may use the average A, described above, as the sum L of distances from a point on the ellipse to the foci. Then, the arithmetic part 210 calculates the pupil diameter from the length (major diameter) of the major axis of the ellipse and the length (minor diameter) of the minor axis (S607). The length $2a$ of the major axis and the length $2b$ of the minor axis can be expressed by the following expressions.

$$2a = L$$

$$2b = 2\sqrt{\left(\frac{L}{2}\right)^2 - c^2}$$

$$= 2\sqrt{\frac{L^2}{4} - \frac{(x2-x1)^2 + (y2-y1)^2}{4}}$$

$$= \sqrt{L^2 - (x2-x1)^2 - (y2-y1)^2}$$

where, L indicates the sum of distances from a point on the edge to the foci, and (x1, y1) and (x2, y2) indicate the foci of the ellipse. When it is assumed, for example, that the pupil diameter $d_p$ is the average of the length $2a$ of the major axis and the length $2b$ of the minor axis, it is expressed in the following way.

$$d_p = a + b$$

$$= \frac{1}{2}\left(L + \sqrt{L^2 - (x2-x1)^2 - (y2-y1)^2}\right)$$

The pupil diameter may be an appropriate value based on the length $2a$ of the major axis and the length $2b$ of the minor axis, such as the length of the minor axis, the length of the major axis, and the mean value of the lengths of the minor axis and the major axis, in addition to the average thereof.

The arithmetic part 210 may, for example, obtain the center position of the pupil based on the foci of the ellipse and/or the lengths of the major axis and the minor axis, further obtain or specify the center of a limbus, and calculate the shift of the center position of the pupil, such as a shift from the center of the limbus. The arithmetic part 210 stores the calculated shift in the memory 240 in association with the pupil diameter.

The arithmetic part 210 may adjust the brightness of the fifth light-source part 91 so as to provide an illumination state which determines the pupil diameter at the environment (such as at an office, a classroom, or at nighttime driving) which the person under measurement desires, other than the illumination state corresponding to the pupil diameter at the daytime. In addition, the pupil diameter at that environment may be measured in advance and used for analysis. In this case, the optimum value at the environment which the person under measurement desires can be analyzed. Instead of executing the processes of steps S601 to S607, the arithmetic part 210 may read measurement data and the pupil diameter stored in advance in the memory 240.

The arithmetic part 210 calculates eye optical-system data based on the pupil diameter and the Hartmann image (S609).

The arithmetic part 210 first uses the Hartmann image obtained in step S601 to detect the center of gravity of each spot. Then, the arithmetic part 210 normalizes the coordinates of the center of gravity detected with the pupil center being used as the origin, by the pupil radius $r_p$, which is half the pupil diameter $d_p$. In other words, the arithmetic part 210 changes the center Ps (X, Y) of gravity within the pupil diameter to Ps $(X/r_p, Y/r_p)$, and the reference grid point $P_{ref}$ $(X_{ref}, Y_{ref})$ corresponding to the center Ps of gravity of a spot of the Hartmann image to $P_{ref}(X_{ref}/r_p, Y_{ref}/r_p)$. An actual wavefront (wavefront where coordinates are not normalized) W (X, Y) is expressed by the following expression.

$$W(X, Y) = \sum_{i=0}^{n}\sum_{j=0}^{i} c_i^{2j-1} Z_i^{2j-1}(X/r_p, Y/r_p)$$

$$= \sum_{i=0}^{n}\sum_{j=0}^{i} c_i^{2j-1} Z_i^{2j-1}(x_s, y_s)$$

where, (X, Y) are coordinates not normalized, and $(x_s, y_s)$ are normalized coordinates.

The arithmetic part 210 uses the normalized coordinates to calculate eye optical-system data such as the Zernike coefficients and ocular aberration. The arithmetic part 210 also stores the data in the memory 240 at appropriate timing.

4-1. Estimating Visual Acuity

Figure 7:
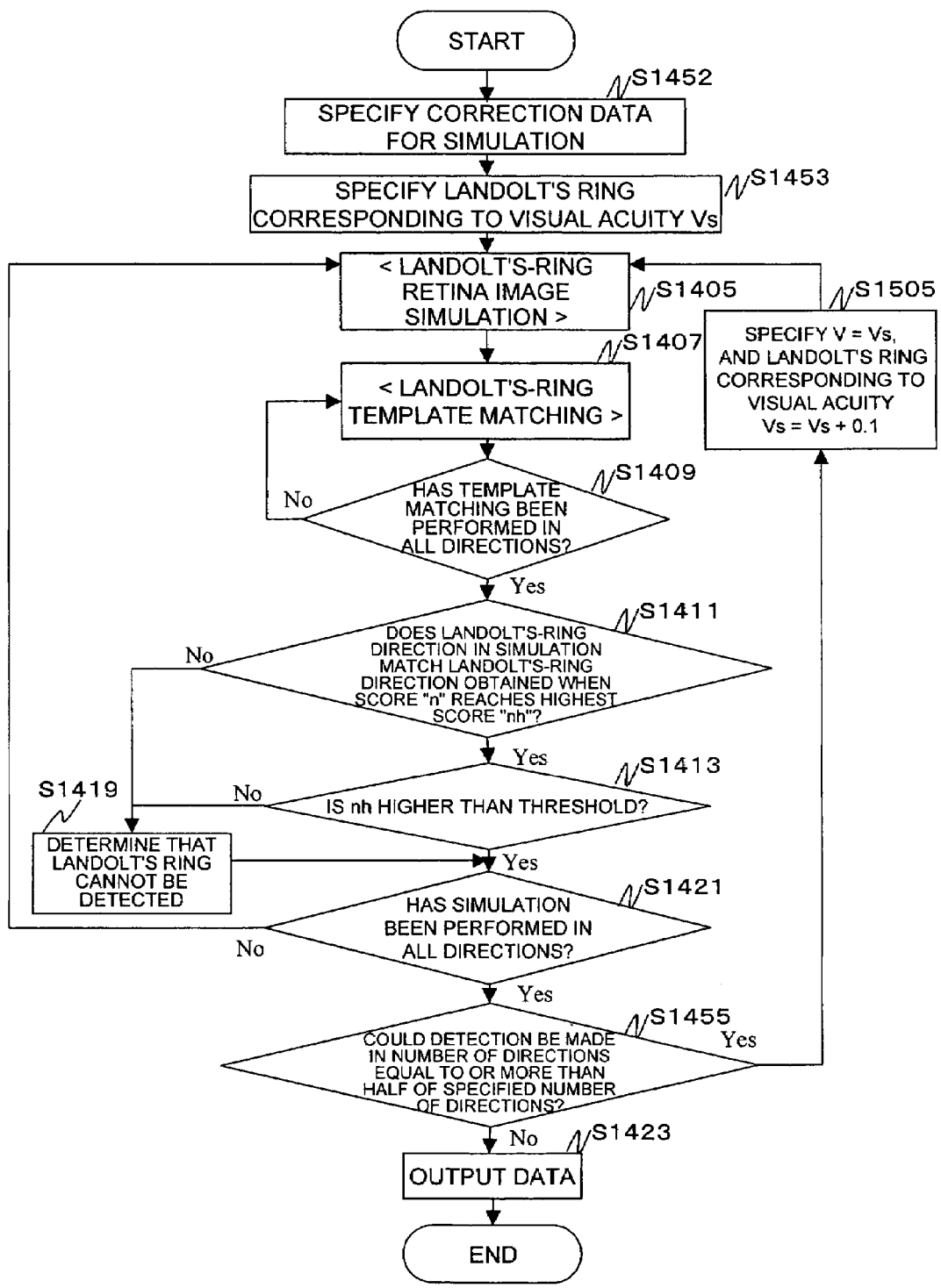
FIG. 7 is a flowchart of visual-acuity simulation performed in steps S107 and S113.

FIG. 7 is a flowchart of the visual-acuity simulation performed in steps S107 and S113. First, the arithmetic part 210 specifies correction data used in simulation (S1452). For example, the arithmetic part 210 can use refractive power or a value calculated based on wavefront aberration, as the correction data. The arithmetic part 210 can set each element of the correction data to zero to estimate the visual acuity of the person under measurement in an environment where correction is not made. In addition, the arithmetic part 210 may specify, for example, the astigmatic power C, the angle A of the astigmatic axis, and/or the spherical power S of the contact lenses currently used.

The arithmetic part 210 specifies a Landolt's ring (S1453) corresponding to visual acuity Vs (for example, Vs=1.0) specified in advance. In this case, the arithmetic part 210 first specifies whether to estimate high-contrast visual acuity or low-contrast visual acuity. For example, the arithmetic part 210 may specify high-contrast visual acuity or low-contrast visual acuity according to an input from the input part 270 or a setting stored in advance in the memory 240. The arithmetic part 210 specifies a Landolt's ring of a high contrast or a low contrast corresponding to the visual acuity Vs specified in advance, according to the setting.

The image-data generation part 211 of the arithmetic part 210 performs Landolt's-ring retinal image simulation to obtain eyesight-target image data (S1405). The image-data generation part 211 first applies simulation to the Landolt's ring in a direction specified in advance (such as a ring having an opening in the upper, lower, right, or left direction). More specifically, the image-data generation part 211 obtains eyesight-target image data which indicates how the Landolt's ring is seen, by simulation according to the wavefront aberration measured in step S105. Specific simulation processing will be described later.

Next, the determination part 212 of the arithmetic part 210 performs Landolt's-ring template matching (S1407). The determination part 212 performs template matching between the eyesight-target image data obtained by the simulation and the Landolt's ring in a certain direction, and stores the direction and a score "n" which indicates the matching degree in the memory 240. A specific process will be described later.

The determination part 212 determines (S1409) whether template matching has been performed in all directions of the Landolt's ring template. If no, the processing proceeds to step S1407, and the matching process is repeated until template matching has been performed in all directions. When yes in step S1409, the determination part 212 determines (S1411) whether the direction of the opening of the Landolt's ring used when the highest score nh is obtained matches the direction of the opening of the Landolt's ring of the eyesight-target image data in the simulation in step S1405. If yes, the determination part 212 determines (S1413) whether the score nh is higher than a threshold specified in advance in the memory 240 or others. The threshold (threshold used to determine whether the Landolt's ring could be identified) can, for example, be a value obtained in the past in contrast with subjective values of a great number of normal eyes.

If no in step S1411 or step S1413, the determination part 212 determines (S1419) that the Landolt's ring cannot be detected, and stores the direction and the fact that the Landolt's ring cannot be detected in the direction, in the memory 240.

After step S1419, or when yes in step S1413, the determination part 212 determines (S1421) whether simulation has been performed in all directions of the simulation Landolt's ring. If no, the processing returns to step S1405, and the arithmetic part 210 repeats the above-described processes in all directions. When yes in step S1421, the determination part 212 further determines whether detection could be made in the number of directions equal to or more than a half of the specified number of directions (S1455).

When yes in step S1455, the correction-factor setting part 213 sets V=Vs, and specifies a Landolt's ring corresponding to visual acuity Vs=Vs+0.1 (S1457). In this case, according to the setting in step S1453, described above, a high-contrast Landolt's ring or a low-contrast Landolt's ring is specified. Then, the processing proceeds to step S1405, and the image-data generation part 211 performs retinal image simulation according to the specified correction factor and Landolt's ring to obtain eyesight-target image data, and the processes of step S1407 and subsequent steps are executed. When no in step S1455, the arithmetic part 210 outputs data (S1423). More specifically, the arithmetic part 210 displays, for example, the current visual acuity V, the detected direction of the Landolt's ring, and the simulation results on the display part 230, and stores them in the memory 240. The arithmetic pat 210 may use decimal visual acuity or log minimum angle resolution (logMAR) visual acuity. The logMAR visual acuity is visual acuity expressed in logarithm of the minimum visible.

FIG. 8 is a flowchart of the retinal image simulation performed in step S1405, described above, when the scattering coefficient is not used. The arithmetic part 210 first calculates a pupil function f(x, y) by the following expression (S204) according to the wavefront aberration W(X, Y) obtained in step S105 shown in FIG. 4 and the specified correction factor.

$$f(x,y)=e^{ikW(X,Y)}$$

The arithmetic part 210 calculates the luminance spread function Land(x, y) of the Landolt's ring (or any image) by referring to the memory 240 (S205). The arithmetic part 210 applies two-dimensional Fourier transform to Land(x, y) to obtain the spatial frequency distribution FR(u, v) (S207). The arithmetic part 210 calculates the spatial frequency distribution OTF of the eye according to the pupil function and multiplies the spatial frequency distribution FR(u, v) of the Landolt's ring (or any image) by the spatial frequency distribution OTF of the eye, as in the following expression to obtain the frequency distribution OR(u, v) after passing through the eye optical system (S209).

$$FR(u,v) \times OTF(u,v) \dashrightarrow OR(u,v)$$

A specific OTF calculation method will be described later.

Next, the arithmetic part 210 applies two-dimensional inverse Fourier transform to OR(u, v) to obtain the luminance spread image LandImage(X, Y) of the Landolt's ring (or any image) (S211).

FIG. 12 is a flowchart of the retinal image simulation performed in step S1405, described above, when the scattering coefficient is used. Steps S204 to S211 are the same as those shown in FIG. 8. The arithmetic part 210 first obtains the PSF corresponding to the Index obtained previously, by referring to the memory 240, and convolution integral the obtained PSF and LandImage (X, Y) to obtain a new simulation image of the retinal image.

FIG. 9 shows an explanatory view indicating the template matching performed in step S1407, described above. As shown in the figure, a template image (lower image) is specified correspondingly to the Landolt's ring original image (upper image), and the template image is stored in association with an identifier indicating the size of the Landolt's ring, in the memory 240. In this example, in the template image, b=1.5a, the number of pixels at a Landolt's-ring block is set to N1, their pixel value is set to 1, the number of pixels at a blurred-point-image block around the Landolt's-ring block is set to N2, and their pixel value is set to −N1/N2. The template image is not limited to this example, and can be appropriately specified. The Landolt's ring original image shown at an upper part of FIG. 9 is a high-contrast Landolt's ring image. Even when a low-contrast original Landolt's ring image is used, the same template image can be used.

Figure 10:
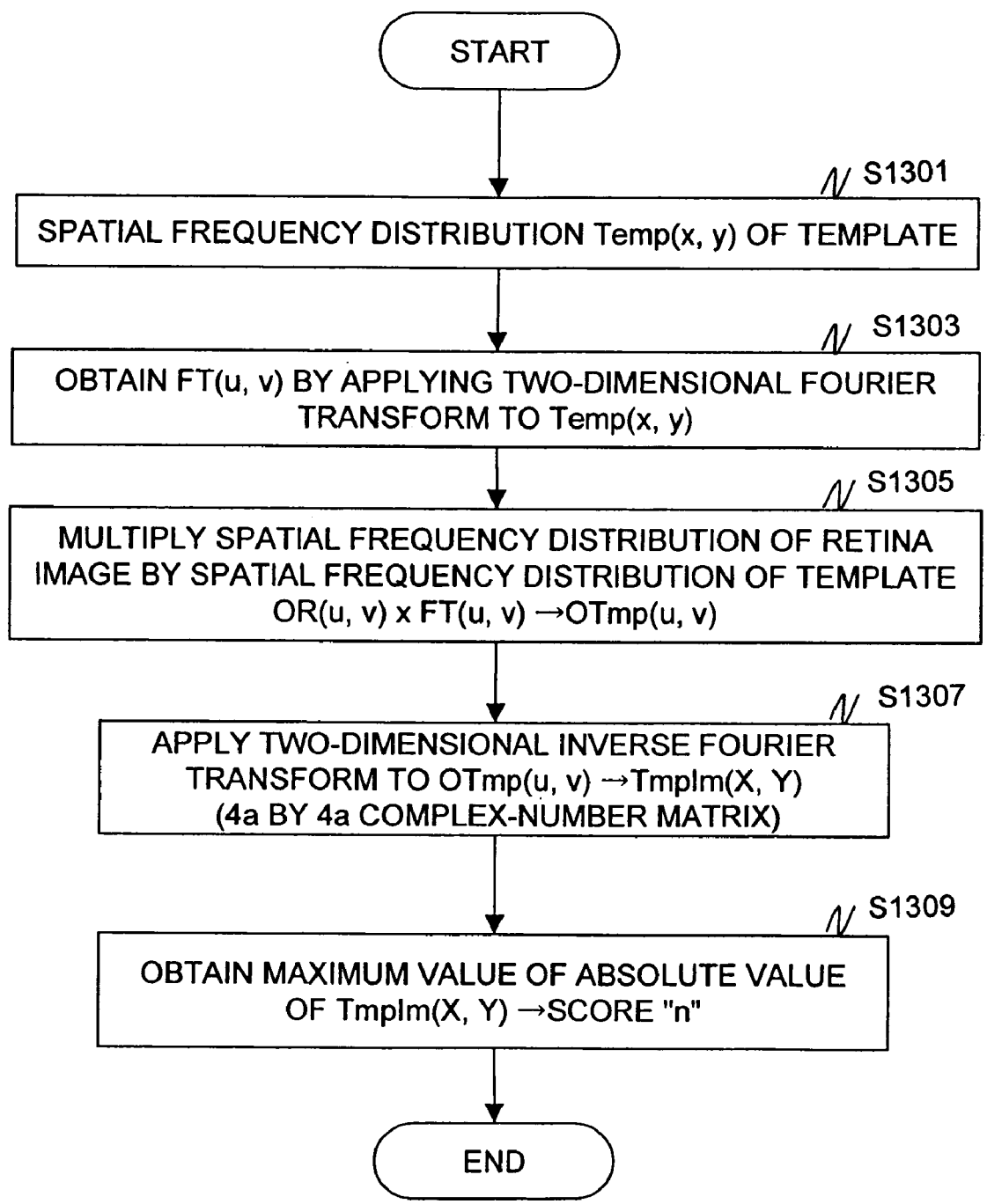
FIG. 10 is a flowchart of Landolt's-ring template matching performed in step S1407.

FIG. 10 is a flowchart of the template matching.

The arithmetic part 210 reads the template image according to the specified size of the Landolt's ring from the memory 240, and obtains its spatial frequency distribution Temp(x, y) (S1301). Then, the arithmetic part 210 applies two-dimensional Fourier transform to Temp(x, y) to obtain FT(u, v) (S1303). The arithmetic part 210 applies two-dimensional Fourier transform to the spatial frequency distribution of the target retinal image data obtained by retinal image simulation to obtain OR(u, v), and multiplies OR(u, v) by the spatial frequency distribution FT(u, v) of the template, as in the following expression, to obtain OTmp(u, v) (S1305).

$$OR(u,v) \times FT(u,v) \dashrightarrow OTmp(u,v)$$

The arithmetic part 210 applies two-dimensional inverse Fourier transform to OTmp(u, v) to obtain TmpIm(X, Y) (4a by 4a complex-number matrix) (S1307). The arithmetic part 210 obtains the maximum value of the absolute values of TmpIm(X, Y), and sets it as a score "n" (S1309).

With such correlation, when the simulation target image is close to the original image, a high score is obtained. If the simulation target image is blurred, the score becomes lower accordingly.

4-2. Contrast Sensitivity

The arithmetic part 210 can calculate contrast sensitivity in the visual-acuity simulation performed in step S107. The arithmetic part 210 obtains Mopt(r, s), the MTF of the eye optical system, based on the wavefront aberration, and calculates contrast sensitivity from the obtained MTF. The arithmetic part 210 also displays the calculated contrast sensitivity on the display part 230 or stores it in the memory 240. The contrast sensitivity can be calculated and displayed in the processing of the flowcharts, described above, instead of being calculated in the process of step S107.

(MTF Calculation)

Next, how the MTF (modulation transfer function) is calculated will be described.

The MTF is an index indicating a spatial-frequency transfer characteristic, and is widely used for expressing the performance of optical systems. How things are seen can be predicted by the MTF, for example, the transfer characteristic of 0 to 100 thick and thin, sine-wave-shaped gratings per one degree obtained. In the present embodiment, a single-color MTF may be used or a white-color MTF may be used, as described below.

First, the single-color MTF is calculated from the wavefront aberration W(x, y). W(x, y) is an input value (measured value), and corneal wavefront aberration obtained from the shape of the cornea can also be used for corneal aberration.

The arithmetic part 210 calculates the pupil function f(x, y) from the wavefront aberration in the following way, when calculates the single-color MTF.

$$f(x,y) = e^{ikW(x,y)}$$

where, i indicates an imaginary number, k indicates a wave vector ($2\pi/\lambda$) and $\lambda$ indicates wavelength.

Here, the arithmetic part 210 multiples $(e^{-arp})^2$ (a is, for example, about 0.05) considering Stiles-Crawford effect. rp is a pupil radius here.

The arithmetic part 210 applies Fourier transform to the pupil function f(x, y) to obtain a point spread function U(u, v) by amplitude.

$$U(u, v) = \int\int_{-\infty}^{\infty} f(x, y) \exp\left[-\frac{i}{R}\frac{2\pi}{\lambda}(ux + vy)\right] dx\, dy$$

where, $\lambda$ indicates a wavelength, R indicates the distance between the pupil to the image point (retina), (u, v) indicates the coordinates of the retina on a plane perpendicular to the optical axis and having the image point O on the retina as the origin, and (x, y) indicates the coordinates of the optical system on the pupil plane.

The arithmetic part 210 multiples the point spread function U(u, v) by amplitude by its complex conjugate to obtain the point spread function (PSF) I(u, v).

$$I(u,v) = U(u,v)U^*(u,v)$$

Next, the arithmetic part 210 applies Fourier transform (or autocorrelation) to the point spread function and standardized to obtain the OTF (optical transfer function), as the following expression.

$$R(r, s) = \int\int_{-\infty}^{\infty} I(u, v) e^{-i2\pi(ru+sv)} du\, dv$$

where, r and s are variables in the spatial-frequency domain.

$$OTF = R(r,s)/R(0,0)$$

Since the magnitude of the OTF is the MTF, the following expression is satisfied.

$$MTF(r,s) = |OTF(u,v)|$$

The white-color MTF is calculated from the single-color MTF, obtained as described above.

To obtain the white-color MTF, the MTF is weighted at each wavelength and added. Since the above-described MTF has a different value at each wavelength, the MTF can be expressed in the following way when the MTF at a wavelength $\lambda$ is indicated by $MTF_\lambda$.

$$MTF(r, s) = \frac{\int \omega_\lambda MTF_\lambda(r, s) d\lambda}{\int \omega_\lambda d\lambda}$$

The MTF is highly weighted at visible-light wavelengths, and the calculation is made.

More specifically, the MTF is obtained in the following way when it is assumed, for example, that the three primary colors (R, G, and B) are specified such that red light has a wavelength of 656.27 nm with a weight of 1, green light has a wavelength of 587.56 nm with a weight of 2, and blue light has a wavelength of 486.13 nm with a weight of 1.

$$MTF(r,s) = (1 \times MTF_{656.27} + 2 \times MTF_{587.56} + 1 \times MTF_{486.13})/(1+2+1)$$

Since the white-light MTF is measured only at one wavelength (840 nm), calibration may be performed for other wavelengths according to the result of measurement, as compensation, to obtain the MTF at each wavelength. More specifically, when the eye optical characteristic measuring apparatus measures eye aberration, for example, at 840 nm, color aberration $W_A(x, y)$ corresponding to a shift from the wavefront aberration $W_{840}(x, y)$ at a wavelength of 840 nm is measured with the use of an eye model, $W_{840}(x, y)$ is added to the color aberration $W_A(X, y)$, and the MTF is calculated at each wavelength from this wavefront aberration in the following way.

$$W_\lambda(x,y) = W_{840}(x,y) + W_A(x,y)$$

(Contrast-Sensitivity Calculation)

The contrast sensitivity will be described next. The contrast sensitivity is expressed by the following equation.

$$S(r, s) = \frac{M_{opt}(r, s)/k}{\sqrt{\frac{4}{T}\left(\frac{1}{X_o^2} + \frac{1}{X_{max}^2} + \frac{u^2}{N_{max}^2}\right)\left(\frac{1}{\eta pE} + \frac{\Phi_0}{1 - e^{-\left(\sqrt{r^2+s^2}/u_0\right)^2}}\right)}}$$

(See Peter G. Barten, "Contrast Sensitivity of the Human Eye and Its Effects on Image Quality" SPIE, December, 1999.)

where, Mopt (r, s) indicates the MTF of the eye optical system, "k" indicates the S/N ratio, which is 3, "T" indicates the weighted time in the neural system, which is 0.1 s, Xo indicates the visual angle of an object, which is 3.8 degrees, Xmax indicates the maximum visual angle in space weighting, which is 12 degrees, Nmax indicates the highest frequency when weighted, which is 15 cycles, η indicates the quantum efficiency of an eye photoreceptor, which is 0.3, "p" indicates the photon conversion coefficient (CRT) of a light source, which is 1.24 (liquid crystal is allowed), "E" indicates a retina illuminance (troland), which is 50 (cdm$^2$)× r$^2$π (mm)=50r$^2$π (td), "r" indicates the pupil radius, which is 100 or less, $\Phi_0$ indicates the spectrum density of neural-system noise, which is 3×108 s·degree$^2$, and u$_0$ indicates a side-suppressed spatial frequency, which is 7 cycles/degree. With the use of this expression, not contrast sensitivity in the eye optical system but contrast sensitivity in the whole vision system with other elements (such as the neural system) taken into account can be predicted.

Figure 11:
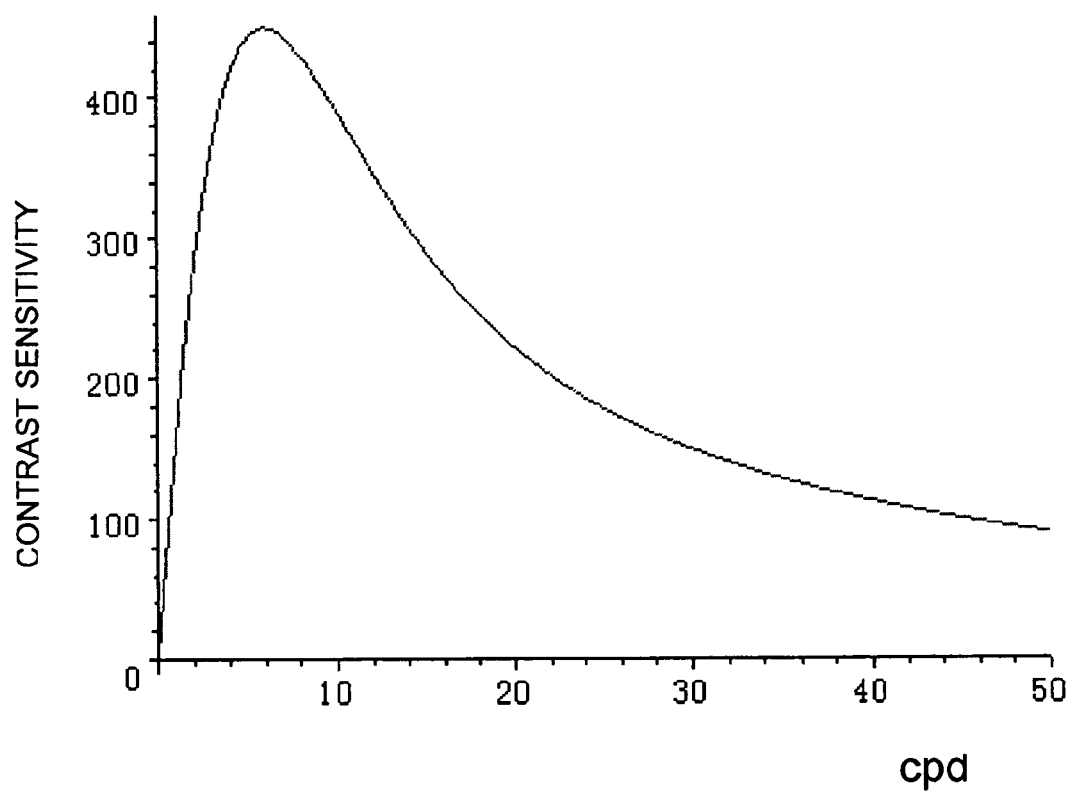
FIG. 11 is a view showing contrast sensitivity.

FIG. 11 is a view showing contrast sensitivity. FIG. 11 shows a one-dimensional graph (obtained, for example, when "s" is 0) at a cross section passing through the origin with the vertical axis indicating the contrast sensitivity calculated by using the foregoing expression and the horizontal axis indicating the spatial frequency. When the contrast sensitivity in the whole vision system corresponding to the spatial frequency is obtained, how a stripe eyesight target is seen, for example, can be predicted.

An ophthalmologist can, for example, compare contrast sensitivity displayed on the display part with sensitivity obtained by subjective measurement. For example, x-direction sensitivity obtained in general subjective measurement with vertical stripe eyesight targets at 3 cpd, 6 cpd, 9 cpd, and 12 cpd can be compared with contrast sensitivity corresponding to each spatial frequency when "s" is set to zero. When contrast sensitivity is rotationally symmetric in polar-coordinate indication, since the contrast sensitivity does not depend on the angle, the contrast sensitivity can be displayed with the horizontal axis indicating the amplitude of the polar coordinate indication.

5. Display Examples

Figure 14:
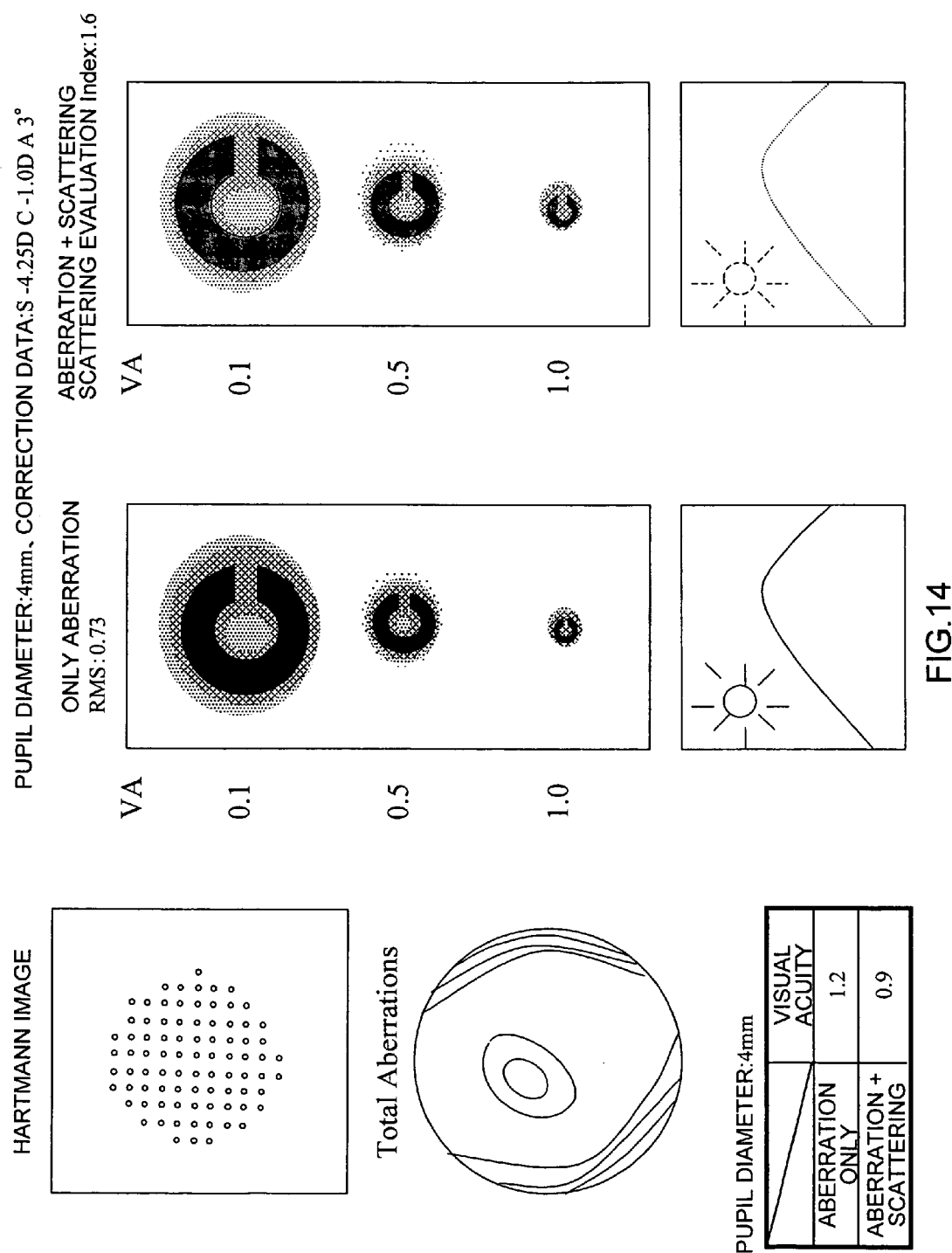
FIG. 14 is a view showing a Hartman image, and RMS values, Index values, visual acuity, and simulation images with aberration only and the aberration and scattering taken into account.
Figure 15:
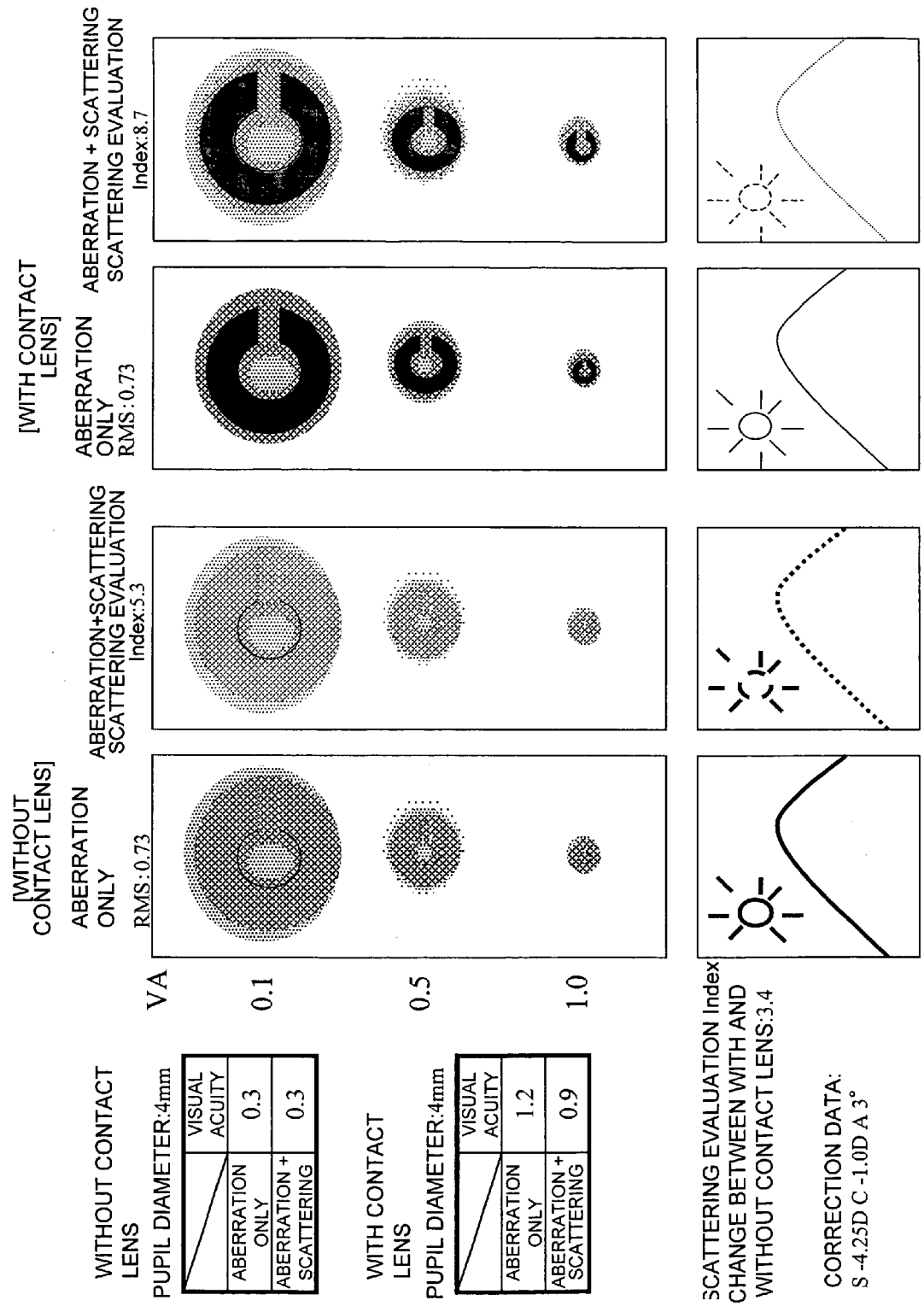
FIG. 15 is a view showing RMS values, Index values, visual acuity, and simulation images with aberration only and the aberration and scattering taken into account, obtained before and after a contact lens is worn.

FIG. 14 shows a Hartmann image, and RMS values, Index values, visual acuity, and simulation images with aberration only and the aberration and scattering taken into account. Since the visual acuity and the simulation image with the aberration only taken into account and the visual acuity and the simulation image with the aberration and scattering, which is one of components other then the aberration, taken into account are displayed in parallel, it is possible to easily determine the effect of the components other than the aberration on how the eye under measurement sees. FIG. 15 shows RMS values, Index values, visual acuity, and simulation images with aberration only and the aberration and scattering taken into account, obtained before and after a contact lens is worn. Since the visual acuity and the simulation image with the aberration only taken into account and the visual acuity and the simulation image with the aberration and scattering, which is one of components other then the aberration, taken into account, obtained before and after the contact lens is worn are displayed in parallel, it is possible to easily determine the effect of the components other than the aberration on how the eye under measurement sees. FIG. 16 shows RMS values, Index values, visual acuity, and simulation images with aberration only and the aberration and scattering taken into account, obtained at a plurality of measurement dates. Since the visual acuity and the simulation images affected by scattering, which is one of components other than the aberration, are displayed time-sequentially, it is possible to easily determine the effect in time of the components other than the aberration on how the eye under measurement sees.

These display examples are obtained by using the flowcharts shown in FIG. 7 and FIG. 8 for usual visual-acuity simulation performed in step S107 of FIG. 4 and by using the flowcharts shown in FIG. 7 and FIG. 12 for visual-acuity simulation with the use of the scattering coefficient, performed in step S113 of FIG. 4.

What is claimed is:

1. An ophthalmological apparatus comprising:
   a first illumination optical system for projecting a point light source on the retina of an eye under measurement;
   a first light-receiving optical system for receiving light reflected from the retina of the eye under measurement through a Hartmann plate;
   a first light-receiving section for converting the received reflected light sent from the first light-receiving optical system into an electrical signal;
   an aberration measurement section for obtaining the aberration of the eye under measurement from the output of the first light-receiving section;
   a components measurement section for obtaining components other than the aberration component, based on a point light-source image caused by each Hartmann plate, from the output of the first light-receiving section;
   a scattering-level calculation section for obtaining a scattering level based on the aberration of the eye under measurement obtained by the aberration measurement section and the components obtained by the component measurement section;
   a data generating section for generating, (1) first data indicating how the eye under measurement sees in a case that a contact lens is worn based on the aberration obtained by the aberration measurement section at a first measurement in which the contact lens is worn, (2) second data indicating how the eye under measurement sees in a case that the contact lens is worn based on the aberration obtained by the aberration measurement section and the scattering level obtained by the scatting-level calculation section, at the first measurement in which the contact lens is worn, (3) third data indicating how the eye under measurement sees in a case that a contact lens is not worn based on the aberration obtained by the aberration measurement section at a second measurement in which the contact lens is not worn, and (4) fourth data indicating how the eye under measurement sees in a case that a contact lens is not worn based on the aberration obtained by the aberration measurement section and the scattering level obtained by the scattering-level calculation section at the second measurement in which the contact lens is not worn; and
   a display section for displaying the first data to the fourth data indicating how the eye under measurement sees, generated by the data generating section.

2. An ophthalmological apparatus according to claim 1, wherein the data generating section references a memory having stored a point spread function (PSF) corresponding to the coefficient expressing the scattering level, obtains the PSF from the coefficient of the obtained scattering level, and executes simulation according to the obtained PSF.

3. An ophthalmological apparatus according to claim 1, wherein
   the data generating section generates a simulation image of a retinal image or how the eye under measurement sees with the measured aberration being taken into account, and a simulation image of a retinal image or how the eye under measurement sees with the measured aberration and the other components, including a scattering component, being taken into account, based on the measurement results obtained by the aberration measurement section and the scattering-level measurement section, and the display section displays the simulation images generated by the data generating section.

4. An ophthalmological apparatus according to claim 1, wherein the data generating section generates an estimated visual-acuity value of how the eye under measurement sees with the measured aberration being taken into account, and an estimated visual-acuity value of how the eye under measurement sees with the measured aberration and the other components, including a scattering component, being taken into account, based on the measurement results obtained by the aberration measurement section and the scattering-level measurement section, and the display section displays the estimated visual-acuity values generated by the data generating section.

5. An ophthalmological apparatus according to claim 1, wherein, when a data of a same eye under measurement is measured a plurality of times, the data generating section generates simulation images and/or data indicating a change in time of the eye under measurement, and the display section displays the simulation images and/or the data generated by the data generating section.

6. An ophthalmological apparatus according to claim 1, wherein the display section displays the data indicating how the eye under measurement sees, based on the measurement result at the state in which the contact lens is not worn and the measurement result at the state in which the contact lens is worn, in a manner in which the data can be compared with each other.

7. An ophthalmological apparatus according to claim 6, wherein the data generating section generates a change in time of the retinal image or data indicating how the eye under measurement sees, and the display section displays the change in time.

8. An ophthalmological apparatus according to claim 1, wherein the data indicating how the eye under measurement sees includes one or any combination of an image and data of an eye optical characteristic, simulation data, and a simulation image.

9. An ophthalmological apparatus according to claim 1, wherein the data generating section is configured as a simulation section for generating simulation images, as the data indicating how the eye under measurements sees, wherein the simulation section generates (1) a first simulation image indicating how the eye under measurement sees in a case that a contact lens is worn based on the aberration obtained by the aberration measurement section at the first measurement in which the contact lens is worn, (2) a second simulation image indicating how the eye under measurement sees in a case that the contact lens is worn based on the aberration obtained by the aberration measurement section and the scattering level obtained by the scattering-level calculation section, at the first measurement in which the contact lens is worn, (3) a third simulation image indicating how the eye under measurement sees in a case that a contact lens is not worn based on the aberration obtained by the aberration measurement section at the second measurement in which the contact lens is not worn, and (4) a fourth simulation image indicating how the eye under measurement sees in a case that a contact lens is not worn based on the aberration obtained by the aberration measurement section and the scattering level obtained by the scattering-level calculation section at the second measurement in which the contact lens is not worn.

10. An ophthalmological apparatus according to claim 9, further comprising:

a memory having stored a point spread function (PSF) corresponding to a coefficient expressing the scattering level;

wherein the simulation section references the memory to obtain the PSF from the coefficient of the obtained scattering level, and executes simulation according to the obtained PSF.

* * * * *